United States Patent
MacQueen et al.

(10) Patent No.: US 7,745,546 B2
(45) Date of Patent: *Jun. 29, 2010

(54) HYDROCARBON-TERMINATED POLYETHER-POLYAMIDE BLOCK COPOLYMERS AND USES THEREOF

(75) Inventors: Richard C. MacQueen, Phillipsburg, NJ (US); Mark S. Pavlin, Savannah, GA (US)

(73) Assignee: Arizona Chemical Company, Jacksonville, FL (US)

( * ) Notice: Subject to any disclaimer, the term of this patent is extended or adjusted under 35 U.S.C. 154(b) by 687 days.

This patent is subject to a terminal disclaimer.

(21) Appl. No.: 11/085,385

(22) Filed: Mar. 21, 2005

(65) Prior Publication Data

US 2005/0165212 A1 Jul. 28, 2005

Related U.S. Application Data

(63) Continuation of application No. 10/142,664, filed on May 8, 2002, now Pat. No. 6,870,011, which is a continuation-in-part of application No. 09/769,081, filed on Jan. 24, 2001, now Pat. No. 6,399,713.

(51) Int. Cl.
C08L 71/02 (2006.01)
(52) U.S. Cl. .................... 525/408; 525/425; 525/432
(58) Field of Classification Search ................ 525/408, 525/425, 432
See application file for complete search history.

(56) References Cited

U.S. PATENT DOCUMENTS

| | | | |
|---|---|---|---|
| 2,410,788 A | 11/1946 | Morgan et al. | |
| 2,663,649 A | 12/1953 | Winkler | |
| 3,037,871 A | 6/1962 | Floyd et al. | |
| 3,131,201 A | 4/1964 | Hovey | |
| 3,156,572 A | 11/1964 | Carlick et al. | |
| 3,957,733 A | 5/1976 | Rogier et al. | |
| 3,962,122 A | 6/1976 | Trial | |
| 4,026,850 A | 5/1977 | Frank et al. | |
| 4,062,819 A | 12/1977 | Mains et al. | |
| 4,066,585 A | 1/1978 | Schepp et al. | |
| 4,165,303 A | 8/1979 | Schlossman et al. | |
| 4,233,170 A | 11/1980 | Genjida et al. | |
| 4,238,582 A | 12/1980 | Deleens et al. | |
| 4,452,922 A | 6/1984 | Speranza et al. | |
| 4,462,926 A | 7/1984 | Prater et al. | |
| 4,581,440 A * | 4/1986 | Coquard et al. | 528/324 |
| 4,717,763 A * | 1/1988 | Coquard et al. | 528/324 |
| 4,735,746 A | 4/1988 | Speranza et al. | |
| 4,740,582 A * | 4/1988 | Coquard et al. | 528/339.3 |
| 4,751,272 A | 6/1988 | Okita et al. | |
| 4,769,423 A | 9/1988 | Risse et al. | |
| 4,778,843 A | 10/1988 | Cooperman et al. | |
| 4,791,157 A * | 12/1988 | Nishizawa et al. | 524/108 |
| 4,795,581 A | 1/1989 | Nieh et al. | |
| 4,830,671 A | 5/1989 | Frihart et al. | |
| 4,839,424 A | 6/1989 | Murabayashi | |
| 4,871,804 A | 10/1989 | Murabayashi | |
| 4,889,560 A | 12/1989 | Jaeger et al. | |
| 4,914,162 A | 4/1990 | Leoni et al. | |
| 4,946,933 A | 8/1990 | Speranza et al. | |
| 5,051,491 A | 9/1991 | Pipper et al. | |
| 5,053,484 A | 10/1991 | Speranza et al. | |
| 5,086,162 A | 2/1992 | Speranza et al. | |
| 5,091,572 A | 2/1992 | Speranza et al. | |
| 5,093,382 A | 3/1992 | Speranza et al. | |
| 5,118,785 A | 6/1992 | Speranza et al. | |
| 5,120,600 A | 6/1992 | Suppiah | |
| 5,124,412 A | 6/1992 | Catena et al. | |
| 5,128,441 A | 7/1992 | Speranza et al. | |
| 5,130,382 A | 7/1992 | Speranza et al. | |
| 5,138,097 A | 8/1992 | Speranza et al. | |
| 5,139,677 A | 8/1992 | Pasternak | |
| 5,140,097 A | 8/1992 | Speranza et al. | |
| 5,143,854 A | 9/1992 | Pirrung et al. | |

(Continued)

FOREIGN PATENT DOCUMENTS

EP 0130927 6/1984

(Continued)

OTHER PUBLICATIONS

Perkins, C; Lai, G. Hydrocarbon Terminated Polyether-Polamide Plock Copolymers in Personal Care and Other Products, IPCOM00012564D from ip.com dated May 14, 2003, pp. 1, 3-7.*
"Jeffamine D-230 Polyoxypropylenediamine" Huntsman Corp., Houstin, TX 1997 CAS Reg. 9046-10-0.
"Jeffamine D-400 Polyoxypropylenediamine" Huntsman Corp., Houston, Tx 1998CAS Reg. 9046-10-0.
"Jeffamine EDR-148 Triethyleneglycoldiamine" Huntsman Corp., Houston, TX 1994 CAS Reg. 929-59-9.
XTJ-502 Poly (Oxyethylene) Diamine,Huntsman Corp., Houston, TX 1996 CAS Reg. 65605-36-9.
"Jeffannine D-2000 Polyoxypropylenediamine," Huntsman Corporation, Houston, TX 1994 [Regarding CAS Reg. No. 9046-10-0].
Sigma-Aldrich Co., Flavors & Frangrances, The Essence of Excellence 2001-2002, Milwaukee, WI., 2001.

(Continued)

*Primary Examiner*—Bernard Lipman
(74) *Attorney, Agent, or Firm*—Gilbreth Roebuck PC; J. M. Gilbreth; Mary A. Gilbreth

(57) ABSTRACT

A composition comprising (a) a resin composition comprising a block copolymer of the formula hydrocarbon-polyether-polyamide-polyether-hydrocarbon; and (b) a polar liquid. The block copolymer may be prepared by a process comprising reacting together reactants comprising dimer acid, diamine, and a polyether having termination at one end selected from amine, hydroxyl and carboxyl, and termination at another end selected from hydrocarbons. The polar liquid may be one or more of an aromatic liquid, a polar aprotic liquid, a ketone-containing liquid, an ester-containing liquid, an ether-containing liquid, an amide-containing liquid and a sulfoxide-containing liquid. The composition may be a gel at room temperature.

31 Claims, No Drawings

U.S. PATENT DOCUMENTS

| | | | |
|---|---|---|---|
| 5,178,646 A | 1/1993 | Barber, Jr. et al. | |
| 5,191,006 A | 3/1993 | Matsumoto et al. | |
| 5,194,638 A | 3/1993 | Frihart et al. | |
| 5,214,124 A * | 5/1993 | Drawert et al. | 528/335 |
| 5,270,353 A | 12/1993 | Nakano et al. | |
| 5,286,288 A | 2/1994 | Tobias et al. | |
| 5,324,812 A | 6/1994 | Speranza et al. | |
| 5,342,918 A * | 8/1994 | Howelton et al. | 528/318 |
| 5,350,789 A | 9/1994 | Sagawa et al. | |
| 5,455,309 A | 10/1995 | Albini et al. | |
| 5,455,326 A | 10/1995 | Parker | |
| 5,500,209 A | 3/1996 | Mendolia et al. | |
| 5,534,575 A * | 7/1996 | Foster et al. | 524/270 |
| 5,585,057 A | 12/1996 | Trotta | |
| 5,589,396 A | 12/1996 | Frye et al. | |
| 5,618,911 A | 4/1997 | Kimura et al. | |
| 5,624,875 A | 4/1997 | Nakanishi et al. | |
| 5,645,632 A | 7/1997 | Pavlin | |
| 5,667,568 A | 9/1997 | Sacripante et al. | |
| 5,804,682 A | 9/1998 | Fischer et al. | |
| 5,807,968 A | 9/1998 | Heinrich et al. | |
| 5,852,118 A | 12/1998 | Horrion et al. | |
| 5,888,597 A | 3/1999 | Frey et al. | |
| 5,902,841 A | 5/1999 | Jaeger et al. | |
| 5,932,630 A | 8/1999 | Kovacs et al. | |
| 5,936,044 A | 8/1999 | Melot et al. | |
| 6,399,713 B1 * | 6/2002 | MacQueen et al. | 525/408 |
| 6,870,011 B2 * | 3/2005 | MacQueen et al. | 525/408 |
| 6,956,099 B2 * | 10/2005 | Pavlin | 528/310 |
| 7,166,656 B2 * | 1/2007 | Majumdar et al. | 523/216 |
| 7,276,547 B2 * | 10/2007 | Pinzon et al. | 524/46 |
| 2007/0269396 A1 * | 11/2007 | Philbin et al. | 424/70.7 |

FOREIGN PATENT DOCUMENTS

| | | |
|---|---|---|
| EP | 0187607 | 12/1985 |
| EP | 0201434 | 3/1986 |
| EP | 0224389 | 11/1986 |
| EP | 0239419 | 3/1987 |
| EP | 0373878 | 12/1989 |
| EP | 0384208 | 2/1990 |
| EP | 0451954 | 3/1991 |
| EP | 0470364 | 7/1991 |
| EP | 0483054 | 9/1991 |
| EP | 0566755 | 4/1992 |
| EP | 0527613 | 8/1992 |
| EP | 0600793 A | 6/1994 |
| GB | 915702 | 1/1963 |
| JP | 61-155426 * | 7/1986 |
| JP | 03-052902 | 3/1991 |
| JP | 09-092328 | 4/1997 |
| JP | 2001-055307 | 2/2001 |
| JP | 2001-261838 | 9/2001 |
| KR | 10-1989-0004334 B1 | 10/1989 |
| WO | WO 88/00603 | 1/1988 |
| WO | WO 90/05910 | 5/1990 |
| WO | WO 97/39151 | 10/1997 |
| WO | 98/17705 | 5/1998 |
| WO | 99/66888 | 12/1999 |
| WO | 02/059181 A2 | 8/2002 |

OTHER PUBLICATIONS

Eastman Chemical Company-2000; http://www.eastman.com/Product_information/ProductHome.asp? EastmanDotCom=True&Product=167. [Accessed Apr. 16, 2000].

* cited by examiner

HYDROCARBON-TERMINATED POLYETHER-POLYAMIDE BLOCK COPOLYMERS AND USES THEREOF

This application is a Continuation of Ser. No. 10/142,664, filed May 8, 2002 now U.S. Pat. No. 6,870,011, which was a CIP of Ser. No. 09/769,081, filed Jan. 24, 2001 now U.S. Pat. No. 6,399,713.

BACKGROUND OF THE INVENTION

1. Field of the Invention

This invention generally relates to organic resins, more particularly to resins having an internal structure comprised of polyamide and polyether, and terminal structure comprised of hydrocarbon. The invention also relates to the preparation of these resins, and their use as, for example, gelling agents for liquids.

2. Description of the Related Art

In many commercially important compositions, the consistency of the product is critical to its commercial success. One example is personal care products, which generally contain one or more active ingredients within a carrier formulation. While the active ingredient(s) determine the ultimate performance properties of the product, the carrier formulation is equally critical to the commercial success of the product in that it largely determines the consistency of the product. The rheology of the carrier (also referred to as the "base") largely determines the flow properties of the product, and the flow properties largely determine the manner in which the consumer will apply or use the product.

For example, aluminum chlorohydrate, aluminum-zirconium tetrachlorohydrate, aluminum-zirconium polychlorohydrate complexed with glycine, and aluminum-zirconium complexed with any of trichlorohydrate, octachlorohydrate, and sesquichlorohydrate are metal salts that are commonly used as active ingredients in deodorant and antiperspirant products. Consumers have shown a preference for applying deodorant from a stick form. Thus, the carrier in a stick-form deodorant must be a relatively hard substance, and waxy fatty alcohol such as stearyl alcohol has often been used as the carrier in these products. As another example, the active ingredient in a lipstick is the colorant. A lipstick should not be as hard as a stick deodorant, but of course must maintain its shape when undisturbed at room temperature. A blend of wax and oil is known to provide a consistency that is well suited as a carrier for a lipstick. As a final example, shampoo desirably has a viscosity greater than water, and when the active ingredient(s) in a shampoo does not have a sufficiently high viscosity, a somewhat viscous carrier material is desirably included in the shampoo formulation.

From the above examples, it is seen that formulators of personal care products depend upon the availability of materials having various rheological properties, in order to formulate a successful personal care product. Materials which have a gel-like character, in that they maintain their shape when undisturbed but flow upon being rubbed, are often desired for personal care products.

Transparent (i.e., clear) carriers are desired by formulators who develop a personal care product wherein colorant is an active ingredient, because a transparent carrier (as opposed to an opaque carrier) will minimally, if at all, interfere with the appearance of the colorant. In recent years, consumers have demonstrated an increasing preference for transparent and colorless personal care products such as deodorants and shampoos. There is thus an increasing demand for transparent materials that can provide the rheological properties needed for various personal care products, and particularly which can impart gel-like character to a formulation.

Polyamide resin prepared from polymerized fatty acid and diamine is reported to function as a gellant in formulations developed for personal care products. For example, U.S. Pat. No. 3,148,125 is directed to a clear lipstick carrier composition formed from polyamide resin compounded with a lower aliphatic alcohol and a so-called "polyamide solvent." Likewise, U.S. Pat. No. 5,500,209 is directed to forming a gel or stick deodorant, where the composition contains polyamide gelling agent and a solvent system including monohydric or polyhydric alcohols. Thus, the prior art recognizes to blend certain polyamides with alcohols, to thereby form a gel.

Polar solvents, e.g., ether- and hydroxyl-containing materials which are liquid at or slightly above room temperature, are desirably included in personal care formulations because they are often benign, allow dilution with at least some water, dissolve a wide range of active and inactive formulation ingredients and are relatively inexpensive. Polar solvents are also available in a wide variety of viscosities and grades. However, these solvents typically do not have the rheological properties that are desired in a carrier, e.g., they do not naturally exhibit gel-like character. Furthermore, gellants for this type of solvent are uncommon and often unavailable.

Accordingly, there is a need in the art for materials that can be combined with solvents, and particularly polar solvents, to afford a transparent material that has gel-like character. The present invention provides this and related advantages as described herein.

BRIEF SUMMARY OF THE INVENTION

In one aspect, the present invention provides a composition comprising (a) a resin composition comprising a block copolymer of the formula hydrocarbon-polyether-polyamide-polyether-hydrocarbon; and (b) a polar liquid. For example, the composition may include a block copolymer wherein the polyether block comprises the formula $-(R^2-O-)$ where $R^2$ is a hydrocarbon; the polyamide block comprises the formula

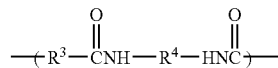

where $R^3$ is a hydrocarbon and $R^4$ is selected from hydrocarbons and polyethers; and the hydrocarbon termini are independently selected from $C_{1-22}$ hydrocarbon radicals. As another example, the composition may include a block copolymer of the formula

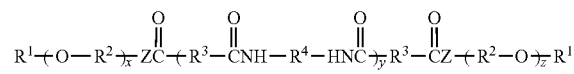

wherein, independently at each occurrence, $R^1$ is a $C_{1-22}$ hydrocarbon radical; $R^2$ is a $C_{2-6}$ hydrocarbon diradical; and $R^3$ is a $C_{2-52}$ hydrocarbon diradical, where at least 50% of the $R^3$ diradicals have at least 34 carbons; $R^4$ is selected from $C_{2-36}$ hydrocarbon diradicals and $C_{4}$-$C_{100}$ polyether diradicals; Z is selected from O and NH; x is an integer from 2 to 100; y is an integer from 1 to 10; and z is an integer from 2 to 100. As another example, the composition may include a block copolymer of the formula

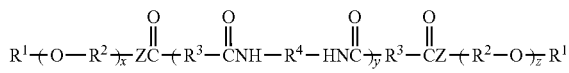

wherein, independently at each occurrence, $R^1$ is a $C_{1-22}$ hydrocarbon radical; $R^2$ is a $C_{2-6}$ hydrocarbon diradical; $R^3$ is a $C_{2-52}$ hydrocarbon diradical, where at least 50% of the $R^3$ diradicals are 1,4-cyclohexane diradical; $R^4$ is selected from $C_{2-36}$ hydrocarbon diradicals and $C_4$-$C_{100}$ polyether diradicals; Z is selected from O and NH; x is an integer from 2 to 100; y is an integer from 1 to 10; and z is an integer from 2 to 100. When 1,4-CHDA contributes more than about 50% of the acid equivalents, then it is preferred that few or none of the $R^4$ groups have less than 6 carbons. As another example, the resin composition may comprise a hydrocarbon-polyether-polyamide-polyether-hydrocarbon block copolymer of the formula

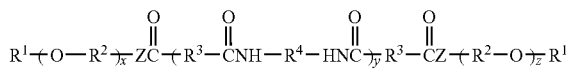

wherein, independently at each occurrence, $R^1$ is a $C_{1-8}$ hydrocarbon radical; $R^2$ is a $C_{2-4}$ hydrocarbon diradical; $R^3$ is a $C_{2-52}$ hydrocarbon diradical, where at least 50% of the $R^3$ diradicals are derived from dimer acid; $R^4$ is selected from $C_{2-8}$ hydrocarbon diradicals and polyether diradicals of the formula —$(R^{11}$—$O)_g$—$R^{11}$— wherein $R^{11}$ is a $C_2$-$C_6$ hydrocarbon diradical independently selected at each occurrence and g is an integer from 2 to 100; Z is selected from O and NH; x is an integer from 2 to 100; y is an integer equal to 1 or more that provides a copolymer molecular weight of 2,000 to 50,000, and z is an integer from 2 to 100. As another example, the composition may include a block copolymer prepared by a process comprising reacting together reactants comprising dimer acid, diamine, and a polyether having termination at one end selected from amine, hydroxyl and carboxyl, and termination at another end selected from hydrocarbons. As another example, the composition may include a block copolymer prepared by a process comprising reacting together reactants comprising diamine, cyclohexane-dicarboxylic acid, and a polyether having termination at one end selected from amine, hydroxyl and carboxyl, and termination at another end selected from hydrocarbon. As another example, the hydrocarbon-polyether-polyamide-polyether-hydrocarbon block copolymer may be prepared by a process comprising reacting together reactants comprising dimer acid, polyetherdiamine, alkylenediamine, and a monofunctional polyether having both hydrocarbon termination and termination selected from amine, hydroxyl and carboxyl, under reaction conditions that form the block copolymer.

In each of the compositions identified above, and identified elsewhere herein, in one aspect the polar liquid is one or more of an aromatic liquid, a polar aprotic liquid, a ketone-containing liquid, an ester-containing liquid, an ether-containing liquid, an amide-containing liquid and a sulfoxide-containing liquid. The composition may be a liquid, which will typically be the case at elevated temperatures. The composition may alternatively be a gel, which will typically be the case at room temperature. Even when the composition is in the gel state, the polar liquid of the composition will be deemed to be a "liquid", i.e., a fluid, even if the composition does not demonstrate syneresis. In fact, the composition preferably does not demonstrate syneresis. The polar liquid within the composition of the present invention will be considered to be a "liquid" for purposes of the present invention, even though the composition demonstrates a gel consistency.

In one aspect, the polar liquid is an ester-containing liquid having a formula selected from $R^6$—$CO_2$—$R^6$ and $R^6$—$CO_2$—$R^7$—$CO_2$—$R^6$ wherein $R^6$ and $R^7$ are organic moieties having 1-12 carbons, where two $R^6$ moieties in a liquid may be joined together to provide a lactone, and a $R^6$ and $R^7$ moiety in a liquid may be joined together to form a lactone. For example, $R^6$ may be selected from $C_1$-$C_{12}$ alkyl, $C_1$-$C_{12}$ hydroxy-substituted alkyl, $C_1$-$C_{12}$ alkoxy-substituted $C_1$-$C_{12}$ alkyl, $C_6$-$C_{12}$ aryl-substituted $C_1$-$C_{12}$ alkyl, $C_1$-$C_{12}$ alkenyl, $C_1$-$C_{12}$ hydroxyalkenyl, $C_1$-$C_{12}$ alkoxy-substituted $C_1$-$C_{12}$ alkenyl, $C_6$-$C_{12}$ aryl, $C_1$-$C_{12}$ alkyl-substituted $C_6$-$C_{12}$ aryl, $C_6$-$C_{12}$ hydroxy-substituted aryl, $C_6$-$C_{12}$ alkoxy-substituted $C_6$-$C_{12}$ aryl; and $R^7$ may be selected from $C_1$-$C_{12}$ alkylene, $C_1$-$C_{12}$ hydroxy-substituted alkylene, $C_2$-$C_{12}$ alkenylene, $C_6$-$C_{12}$ arylene, $C_6$-$C_{12}$ hydroxy-substituted arylene, $C_1$-$C_{12}$ alkoxy-substituted $C_6$-$C_{12}$ arylene. As another example, the ester-containing liquid may be selected from the group consisting of ethyl lactate, butyl propionate, dibutyl adipate, ethoxyethyl propionate, butyl acrylate, vinyl propionate, butyl acetate, dibutyl sebacate, diethylphthalate, vinyl acetate, methyl methacrylate, ethyl acetate, ethyl hexyl acetate, and gamma-butyrolactone.

In another aspect, the polar liquid is an aromatic liquid. For example, the aromatic liquid may be selected from the group consisting of benzene, toluene, o-xylene, m-xylene, p-xylene, styrene, alpha-methyl styrene, ($C_1$-$C_{18}$ alkyl)-benzoate, ($C_1$-$C_{18}$ alkyl)salicylate, and ($C_1$-$C_{12}$ alkyl)($C_1$-$C_{12}$ alkyl)phthalate.

In another aspect, the polar liquid is a polar aprotic liquid. For example, the polar aprotic liquid may be selected from the group consisting of N-methylpyrrolidinone, propylene carbonate, tetrahydrofuran, dimethyl sulfoxide, methylene chloride, and dichloroethane.

In another aspect, the polar liquid is a ketone-containing liquid. For example, the ketone-containing liquid may have the formula $R^6$—C(=O)—$R^6$ wherein $R^6$ at each occurrence is independently selected from organic moieties having 1-12 carbons, where two $R^6$ moieties in a liquid may be joined together to provide a cyclic ketone. For further example, the ketone-containing polar liquid may be selected from acetone, methyl ethyl ketone, methyl isobutyl ketone and cyclohexanone.

In another aspect, the polar liquid is a sulfoxide-containing liquid. For example, the sulfoxide-containing liquid may have the formula $R^8$—S(=O)—$R^8$ and $R^8$ is independently selected at each occurrence from $C_1$-$C_6$ alkyl.

In another aspect, the polar liquid is a glycol ether. For example, the polar liquid may be a glycol ether of the formula $R^9$—[O—$R^{10}$—]$_n$—OH wherein $R^9$ is a $C_1$-$C_{22}$ hydrocarbon, $R^{10}$ is a $C_2$-$C_6$ hydrocarbon independently selected at each occurrence, and n is an integer selected from 1, 2, 3, 4, 5 and 6. As another example, the glycol ether may be ethylene glycol mono phenyl ether, dipropyleneglycol mono methyl ether or tripropyleneglycol mono methyl ether.

In another aspect, the polar liquid may include, or may exclusively be, a liquid fragrance. Liquid fragrances are well known in the art and are sold by many companies.

In another aspect, the polar liquid may include, or may exclusively be, a liquid surfactant. Liquid surfactants are well known in the art and are sold by many companies.

In another aspect, the polar liquid may include, or may exclusively be, a liquid polyepoxy resin. Liquid polyepoxy resins are well known in the art and are sold by many companies.

In another aspect, the present invention provides a hydrocarbon-polyether-polyamide-polyether-hydrocarbon block copolymer of the formula

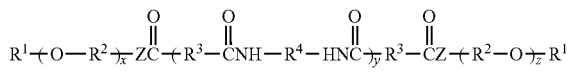

wherein, independently at each occurrence, $R^1$ is a $C_{1-8}$ hydrocarbon radical; $R^2$ is a $C_{2-4}$ hydrocarbon diradical; $R^3$ is a $C_{2-52}$ hydrocarbon diradical, where at least 50% of the $R^3$ diradicals are derived from dimer acid; $R^4$ is selected from $C_{2-8}$ hydrocarbon diradicals and polyether diradicals of the formula $—(R^{11}—O)_g—R^{11}—$ wherein $R^{11}$ is a $C_2$-$C_6$ hydrocarbon diradical independently selected at each occurrence and g is an integer from 2 to 100; Z is selected from O and NH; x is an integer from 2 to 100; y is an integer equal to 1 or more that provides a copolymer molecular weight of 2,000 to 50,000, and z is an integer from 2 to 100. This block copolymer may be combined with a polar liquid as described herein.

In another aspect, the present invention provides a hydrocarbon-polyether-polyamide-polyether-hydrocarbon block copolymer prepared by a process comprising reacting together reactants comprising dimer acid, polyetherdiamine, alkylenediamine, and a monofunctional polyether having both hydrocarbon termination and termination selected from amine, hydroxyl and carboxyl, under reaction conditions that form the block copolymer. In further aspects, the present invention provides that the polyetherdiamine and the monofunctional polyether in total contribute 20-45 wt % of the total weight of the reactants; the polyetherdiamine has the formula $H_2N—(R^{11}—O)_g—R^{11}—NH_2$ wherein $R^{11}$ is a $C_2$-$C_6$ hydrocarbon diradical independently selected at each occurrence, g is an integer from 2 to 50, and the polyetherdiamine contributes 10-30 wt % of the total weight of the reactants; the monofunctional polyether has the formula $R^1—O—(R^{11}—O)_h—R^{11}—NH_2$ wherein $R^1$ is a $C_{1-6}$ hydrocarbon radical, $R^{11}$ is a $C_2$-$C_6$ hydrocarbon diradical independently selected at each occurrence, h is an integer from 2 to 50, and the monofunctional polyether contributes 5-20 wt % of the total weight of the reactants; the polyetherdiamine has the formula $H_2N—(R^{11}—O)_g—R^{11}—NH_2$ wherein $R^{11}$ is a $C_2$-$C_4$ hydrocarbon diradical independently selected at each occurrence from ethylene, propylene and butylene, g is an integer from 2 to 50, and the polyetherdiamine contributes 10-30 wt % of the total weight of the reactants, and the monofunctional polyether has the formula $R^1—O—(R^{11}—O)_h—R^{11}—NH_2$ wherein $R^1$ is a $C_{1-6}$ hydrocarbon radical, $R^{11}$ is a $C_2$-$C_4$ hydrocarbon diradical independently selected at each occurrence from ethylene, propylene and butylene, h is an integer from 2 to 50, and the monofunctional polyether contributes 5-20 wt % of the total weight of the reactants, and the alkylenediamine has the formula $H_2N—R^{11}—NH_2$ wherein $R^{11}$ is a $C_2$-$C_6$ hydrocarbon diradical; and wherein dimer acid, polyetherdiamine, alkylenediamine, and monofunctional polyether in total constitute at least 75 wt % of the total weight of the reactants. This block copolymer may be combined with a polar liquid according to the present invention, to provide gelled structures.

In another aspect, the present invention provides composition comprising polar liquid and block copolymer where the composition is either in a gel form or is at elevated temperature, i.e., a temperature greater than room temperature (typically ca. 21° C.) and is in a liquid but upon cooling to room temperature the liquid composition will adopt a gel form.

These and related aspects of the present invention are described more fully herein.

DETAILED DESCRIPTION OF THE INVENTION

In one aspect, the present invention provides a hydrocarbon-terminated block copolymer of the formula (1)

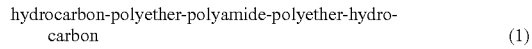

In formula (1), a hydrocarbon group contains only carbon and hydrogen atoms. A polyether groups contains 2 or more ether groups, i.e., groups of the formula hydrocarbon-O-hydrocarbon, where the hydrocarbon of one ether group can also serve as the hydrocarbon of another ether group. A polyamide group contains 2 or more amide groups, i.e., groups of the formula hydrocarbon-C(=O)—NR-hydrocarbon, where the hydrocarbon of one amide group may, or may not, also serve as the hydrocarbon of another amide group, and R is hydrogen or a hydrocarbon. Essentially, R in the amide group is determined by the choice of diamine used in the preparation of the polyamide block of the block copolymer of the present invention. In one aspect, at least one amide group of the polyamide is flanked by polyether groups, while in another aspect all of the amide groups in the polyamide block are flanked by hydrocarbon groups.

Suitable hydrocarbon groups are formed from one or more of aliphatic and aromatic moieties. Suitable aliphatic moieties are alkyl, alkylene, alkenyl, alkenylene, alkynyl, alkylnylene, cycloalkyl, cycloalkylene, cycloalkenyl, cycloalkenylene, cycloalkynyl, and cycloalkynylene moieties. Aromatic moieties are also referred to herein as aryl groups. The hydrocarbon groups that terminate the block copolymers of the present invention will be referred to herein as $R^1$.

As used herein, alkyl, alkenyl, alkynyl, cycloalkyl, cycloalkenyl, and cycloalkynyl are monovalent radicals, while alkylene, alkenylene, alkynylene, cycloalkylene, cycloalkenylene, and cycloalkynylene are polyvalent radicals. As used herein alkyl, alkylene, cycloalkyl, and cycloalkylene are saturated radicals, while alkenyl, alkenylene, alkynyl, alkylnylene, cycloalkenyl, cycloalkenylene, cycloalkynyl, and cycloalkynylene are unsaturated radicals. The alkyl, alkylene, alkenyl, alkenylene, alkynyl, and alkynylene moieties may be straight chain or branched. The cycloalkyl, cycloalkenyl, cycloalkynyl, cycloalkylene, cycloalkenylene and cycloalkynylene moieties may be monocyclic or polycyclic, where a polycyclic moiety may be, for example, bicyclic or tricyclic.

Exemplary alkyl moieties are methyl, ethyl, propyl, hexyl, and 2-ethylhexyl. Exemplary alkylene moieties are methylene (—$CH_2$—), methylidene (=$CH_2$), and ethylene (—$CH_2CH_2$—). Exemplary cycloalkyl groups are cyclohexyl and norbornyl.

Suitable aromatic moieties are monocyclic or polycyclic. An exemplary monocyclic aryl group is phenyl, while exemplary polycyclic aryl groups are naphthyl and fulverenyl. The aromatic moiety may be monovalent, e.g., phenyl, or polyvalent, e.g., phenylene.

The hydrocarbon group may be a combination of aromatic and aliphatic groups. For example, benzyl (phenyl-$CH_2$—, an arylalkylene group), tolyl ($CH_3$-phenylene-, an alkylarylene group), and xylyl (($CH_3)_2$-phenylene-, a dialkylarylene group). The hydrocarbon group may be a combination of two or more aromatic groups, e.g., biphenyl (phenyl-phenylene-, an arylarylene group).

The $R^1$ group necessarily contains at least one carbon. In one embodiment, the $R^1$ group contains 1-32 carbons. In one embodiment, the $R^1$ alkyl group contains 1-12 carbons. In one embodiment, $R^1$ is an alkyl group containing 1-4 carbons. In one embodiment, the $R^1$ group is an alkyl group. In one embodiment, the $R^1$ alkyl group is straight-chained. In one embodiment, the $R^1$ alkyl group is branched. In one embodiment, $R^1$ is methyl.

The block copolymer of formula (1) contains at least two polyether blocks. As its name implies, a polyether block contains a plurality of ether groups, i.e., groups of the formula —C—O—C—. In other words, a polyether block contains the repeating formula —O—$R^2$— where $R^2$ is a hydrocarbon group. In one aspect, $R^2$ is an alkylene group. The alkylene group $R^2$ may be aliphatic (saturated and/or unsaturated) or aromatic, straight chain and/or branched, independently at each occurrence in the polyether block. In one aspect, $R^2$ has 1-6 carbons at each occurrence in the polyether block, while in another aspect $R^2$ has 2-4 carbons at each occurrence. In one aspect, $R^2$ has the formula —$CH_2$—$CH(R^{2a})$— wherein $R^{2a}$ is selected from hydrogen, methyl and ethyl.

In one aspect, the polyether component of the block copolymer has a molecular weight (measured as either number or weight average) of less than 10,000. In another aspect, the molecular weight is between 100 and 4,000.

The block copolymer of formula (1) contains a polyamide block. As its name implies, the polyamide block contains a plurality of amide groups, i.e., groups of the formula —NH—C(=O)— and/or —C(=O)—NH—. In the polyamide block, two or more amide groups are separated by hydrocarbon groups, e.g., alkylene groups and/or polyether groups.

In one aspect, the polyamide block contains —C(=O)—$R^3$—C(=O)— moieties wherein $R^3$ is a hydrocarbon group. In one aspect, the polyamide block includes $R^3$ groups having at least 30 carbons. In one aspect, the polyamide block includes $R^3$ groups having 30-42 carbons.

In one aspect, the polyamide block includes $R^3$ groups that are formed from fatty acid polymerization. Fatty acids derived from vegetable oils, tallow, and tall oil (the latter are known as tall oil fatty acids, or TOFA) are commonly subjected to thermal polymerization, typically in the presence of a clay catalyst, to provide a commercially-available product known as dimer acid. These fatty acids contain 18 carbons, so that corresponding dimer acid consists mainly of $C_{36}$ dicarboxylic acids. This dimer acid may be denoted by the structure HOOC—$C_{34}$—COOH, where the $C_{34}$ group is an exemplary $R^3$ group of the present invention. $C_{34}$ is a mixture of isomeric structures, as more fully described in detailed descriptions of dimer acid, as found in, for example, *Naval Stores—Production, Chemistry and Utilization*, D. F. Zinkel and J. Russel (eds.), Pulp. Chem. Assoc. Inc., 1989, Chapter 23.

Suitable polymerized fatty acids are available commercially as, for example, UNIDYME™ dimer acid, from Arizona Chemical, company of International Paper, (Jacksonville, Fla.), EMPOL™ dimer acid from Henkel Corporation (now Cognis @cognis.com, Cincinnati, Ohio); and PRIPOL™ dimer acid from Unichema North America (Chicago, Ill.).

Dimer acid, as commercially available, typically contains some by-products of the fatty acid polymerization process. One common byproduct is so-called trimer acid, which results when three fatty acid molecules react together to form a $C_{64}$ tricarboxylic acid. It may happen, in the preparation of a block copolymer of the present invention, that two of the carboxylic acid groups of trimer acid will react with, e.g., a diamine, leaving one carboxylic acid group unreacted. When this occurs, the block copolymer will contain a carboxylic acid-substituted $R^3$ group, which is technically not a hydrocarbon. Accordingly, while block copolymers of the present invention contain hydrocarbon groups between two NHC(=O) groups, they may also contain some, typically a minor amount, of carboxylic acid-substituted hydrocarbon groups between two NHC(=O) groups. For convenience, as used herein, $C_{34}$ refers to the incorporation of dimer acid into a polyamide block, where $C_{34}$ includes the reaction product of some trimer acid that may be a by-product in the commercial dimer acid.

In one aspect, the present invention provides block copolymers of formula (1) wherein each of the C(=O) groups is bonded to $C_{34}$, i.e., the block copolymer is formed from dimer acid as the exclusive polyacid reactant. However, in another aspect, the polyamide block includes both $C_{34}$ and "co-diacid"-derived $R^3$ groups. Thus, the polyamide block may be formed by reacting both dimer acid and co-diacid with a diamine. However, in a preferred embodiment of the invention, dimer acid is used without any co-diacid in preparing the polyamide block of the block copolymer.

As used herein, a co-diacid is a compound of formula HOOC—$R^3$—COOH where $R^3$ is not $C_{34}$ as defined above. In one aspect, the polyamide block in copolymers of formula (1) includes $R^3$ groups having 2-32 carbons, which are referred to herein a co-diacid $R^3$ groups. Suitable co-diacids have a linear $C_{4-12}$ hydrocarbon group between the two carboxylic acid groups, and more preferably have a linear $C_{6-8}$ hydrocarbon group. Linear diacids suitable for the present invention include 1,6-hexanedioic acid (adipic acid), 1,7-heptanedioic acid (pimelic acid), 1,8-octanedioic acid (suberic acid), 1,9-nonanedioic acid (azelaic acid), 1,10-decanedioic acid (sebacic acid), 1,11-undecanedoic acid, 1,12-dodecanedioic acid (1,10-decanedicarboxylic acid), 1,13-tridecanedioic acid (brassylic acid) and 1,14-tetradecanedioic acid (1,12-dodecanedicarboxylic acid).

Another exemplary co-diacid for use in the present invention is the reaction product of acrylic or methacrylic acid (or the ester thereof, with a subsequent hydrolysis step to form an acid) and an unsaturated fatty acid. For example, a $C_{21}$ diacid of this type may be formed by reacting acrylic acid with a $C_{18}$ unsaturated fatty acid (e.g., oleic acid), where an ene-reaction presumably occurs between the reactants. An exemplary $C_{21}$ diacid is commercially available from Westvaco Corporation, Chemical Division, Charleston Heights, S.C., as their product number 1550.

Aromatic diacids may be used as the co-diacid. An "aromatic diacid" as used herein is a molecule having two carboxylic acid groups (—COOH) or reactive equivalents thereof (e.g., acid chloride (—COCl) or ester (—COOR)) and at least one aromatic ring ("Ar"). Phthalic acids, e.g., isophthalic acid and terephthalic acid, are exemplary aromatic diacids. The aromatic diacid may contain aliphatic carbons bonded to the aromatic ring(s), as in HOOC—$CH_2$—Ar—$CH_2$—COOH and the like. The aromatic diacid may contain two aromatic rings, which may be joined together through one or more carbon bonds, (e.g., biphenyl with carboxylic acid substitution) or which may be fused (e.g., naphthalene with carboxylic acid substitution).

In one aspect, the $C_{34}$ $R^3$ groups constitute at least 50 mol % of the total of the $R^3$ groups. In other aspects, the $C_{34}$ $R^3$ groups constitute at least 60 mol %, or 70 mol %, or 80 mol %, or 90 mol %, or 95 mol % of the $R^3$ groups. Stated another way, dimer acid contributes at least 50% of the diacid equivalents, or at least 60-%, or 70%, or 80%, or 90%, or 95% of the diacid equivalents in the polyamide block of the copolymer of formula (1). In one aspect of the invention, only dimer acid is used to form the block copolymer, i.e., no co-diacid is among the reactants.

As mentioned above, in one aspect of the present invention, the polyamide block contains —C(=O)—$R^3$—C(=O)— moieties wherein $R^3$ is a hydrocarbon group. As discussed above, in a preferred aspect the polyamide block includes $R^3$ groups having at least 30 carbons, more preferably the polyamide block includes $R^3$ groups having 30-42 carbons, and still more preferably includes $R^3$ groups that have the structure of dimer acid with the exception that the carboxylate groups are missing. While in a preferred aspect of the invention the polyamide block is prepared from dimer acid, optionally with co-diacid, in another preferred aspect of the invention the polyamide block is prepared without dimer acid, i.e., is prepared with only co-diacid.

In one aspect of the invention, the polyamide block contains the cyclohexane diradical between at least two carbonyl groups. The carbonyl groups are preferably located at opposite carbons of the cyclohexane group, i.e., the $R^3$ cyclohexane group has the following structure (2)

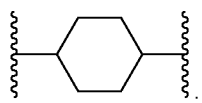

(2)

In one aspect, all of the $R^3$ groups in the block copolymer contain the cyclohexyl group (2). In another aspect, at least 50% of the $R^3$ groups in the block copolymer contain the cyclohexyl group (2). In another aspect, at least 25% of the $R^3$ groups in the block copolymer contain the cyclohexyl group (2). The introduction of an $R^3$ group of structure (2) into a diblock copolymer of the present invention is readily accomplished by including cyclohexanedicarboxylic acid (CHDA) among the copolymer-forming reactants. CHDA, including 1,4-CHDA, is commercially available from many sources, e.g., Aldrich (Milwaukee, Wis.; @sigma-aldrich.com).

In one aspect, the polyamide block contains —NH—$R^4$—NH— moieties wherein $R^4$ is a hydrocarbon group. In one aspect, the $R^4$ hydrocarbon group has 1-20 carbons. In one aspect, the polyamide block includes $R^4$ groups having 1-10 carbons. In one aspect, the $R^4$ group is an alkylene group. In one aspect, $R^4$ is a straight-chained alkylene group. In one aspect, the polyamide block includes $R^4$ groups having 2 carbons, while in another aspect at least 50% of the $R^4$ groups have 2 carbons, while in another aspect all of the $R^4$ groups have 2 carbons.

When the $R^3$ group of the polyamide block is most often the cyclohexane diradical, i.e., when at least 50% of the $R^3$ groups are cyclohexane diradical, then the $R^4$ group preferably has at least 6 carbons. This is because when $R^4$ has only 2-4 carbons, the melting point of the resin tends to increase. Likewise, as more of the $R^3$ groups are cyclohexane diradical, the melting point of the resin tends to increase. Accordingly, when at least about 50% of the $R^3$ groups are cyclohexane diradical, then most if not all of the $R^4$ groups should have at least 6 carbons in order to counteract the melting point-increasing effect of the cyclohexane diradical.

The melting point of the resin should not be too high or else it will be difficult to dissolve the resin in a polar liquid. Typically, the resin and polar liquid are heated until the resin melts, and then the composition is stirred to provide a homogeneous solution at elevated temperature. Upon cooling, this homogenous solution typically forms a gel. When the melting point of the resin exceeds the boiling point of the polar liquid, then the resin cannot be heated to its melting point in the solvent, and dissolution of the resin in the solvent becomes more difficult and time-consuming. Thus, it is preferred that the resin have a melting point of less than about 250° C., more preferably less than about 200° C. In another aspect, it is preferred that the resin have a melting point that is less than, or within about 25° C. of, the boiling point of the polar liquid. When all of the $R^3$ groups in the resin are cyclohexane diradical, and all of the $R^4$ groups have only two carbons, the resulting resin has a melting point in excess of about 300° C., and such a high melting resin is very difficult to dissolve in a polar liquid. Certainly, even when all of the $R^3$ groups are cyclohexane diradical, a very small amount of the $R^3$ groups may have only 2 carbons, and still provide a resin that can be dissolved in many solvents at elevated temperature.

In one aspect, the polyamide block contains —NH—$R^4$—NH— moieties wherein $R^4$ is a polyether group. As defined above, a polyether block contains a plurality of ether groups, i.e., groups of the formula —C—O—C—. In other words, a polyether block contains the repeating formula —O—$R^2$— where $R^2$ is a hydrocarbon group. In one aspect, $R^2$ is an alkylene group. The alkylene group $R^2$ may be aliphatic (saturated and/or unsaturated) or aromatic, straight chain and/or branched, independently at each occurrence in the polyether block. In one aspect, $R^2$ has 1-6 carbons at each occurrence in the polyether block, while in another aspect $R^2$ has 2-4 carbons at each occurrence. In one aspect, $R^2$ has the formula —$CH_2$—CH($R^{2a}$)— wherein $R^{2a}$ is selected from hydrogen, methyl and ethyl.

In one aspect, the polyether component of the $R^4$ potion of the block copolymer of the present invention has a molecular weight (number or weight average) of less than 10,000. In another aspect, the molecular weight is between 100 and 4,000.

Compounds of the formula $H_2N$—$R^4$—$NH_2$ are commonly known as diamines, and are available from a large number of vendors. Compounds of the formula HOOC—$R^3$—COOH are commonly known as diacids, or dibasic acids, and are likewise available from a large number of vendors. Aldrich (Milwaukee, Wis.; @sigma-aldrich.com); EM Industries, Inc. (Hawthorne, N.Y.; @emscience.com); Lancaster Synthesis, Inc. (Windham, N.H.; @lancaster-.co.uk) are three representative vendors.

In formula (1), the bond '—' between hydrocarbon and polyether represents a C—O bond where the carbon is contributed by the hydrocarbon and the oxygen is contributed by the polyether.

In formula (1), in one aspect, the bond between polyether and polyamide is C—NH—C(=O)—C where C—NH may be seen as being contributed by the polyether and C(=O)—C may be seen as being contributed by the terminal acid group of a polyamide. Block copolymers according to this aspect may be formed by, for example, reacting an amino and hydrocarbon terminated polyether of the formula $R^1$—(O—$R^2$—)$NH_2$ with a carboxylic acid terminated polyamide of the formula HOOC—NH—$R^4$—NH-etc. so as to form $R^1$—(O—$R^2$—)N—C(=O)—$R^4$. Thus, an amide group may be present as the link between polyether and polyamide in formula (1).

In formula (1), in one aspect, the bond between polyether and polyamide is C—C(=O)—NH—C where C—C(=O) may be seen as being contributed by the polyether and NH—C may be seen as being contributed by the terminal amine group of a polyamide. Block copolymers according to this aspect may be formed by, for example, reacting a carboxylic acid and hydrocarbon terminated polyether of the formula R$^1$—(O—R$^2$—)COOH with an amine terminated polyamide of the formula H$_2$N—R$^4$—NH—C(=O)—R$^3$- etc. so as to form R$^1$—(O—R$^2$—)—C(=O)—NH—R$^4$—NH—C(=O)—R$^3$-etc. Thus, once again, an amide group may be present as the link between polyether and polyamide in formula (1). However, urethane groups are preferably not a part of the block copolymer of the present invention.

In formula (1), in one aspect, the bond between polyether and polyamide is C—O—C(=O)—C where C—O may be seen as being contributed by the polyether and C(=O) may be seen as being contributed by the terminal acid group of a polyamide. Block copolymers according to this aspect may be formed by, for example, reacting a hydroxyl and hydrocarbon terminated polyether of the formula R$^1$—(O—R$^2$—)OH with a carboxylic acid terminated polyamide of the formula HOOC—NH—R$^4$—NH-etc. so as to form R$^1$—(O—R$^2$—)O—C(=O)—R$^4$. Thus, an ester group may be present as the link between polyether and polyamide in formula (1). In various aspects of the invention, the block copolymer contains 0 ester groups (e.g., when the polyether is amine terminated rather than hydroxyl terminated), or no more than 1 ester group (when a mixture of amine terminated and hydroxyl terminated polyether are used), or no more than 2 ester groups.

In one aspect, the present invention provides a composition comprising a hydrocarbon-terminated polyether-polyamide block copolymer of the present invention having an acid number of less than 25, or less than 20, or less than 15, or less than 10. The hydrocarbon-terminated polyether-polyamide block copolymer of formula (1) does not have any free carboxylic acid groups, and accordingly has an acid number of zero. However, when prepared from diacid, diamine and hydrocarbon-terminated polyether according to a process described herein, some of the diacid may not react with the diamine and/or polyether, and according the final product may have some unreacted carboxylic acid that will be responsible for the product having an acid number greater than zero. Preferably, the product has a minor amount of this unreacted diacid, and thus has only a small acid number. Esterification catalysts may be used to encourage all of the diacid to react with hydroxyl groups, so as to minimize the amount of free acid, i.e., to reduce the acid number of the product.

In one aspect, the present invention provides a composition comprising a hydrocarbon-terminated polyether-polyamide block copolymer of the present invention having an amine number of less than 25, or less than 20, or less than 15, or less than 10, or less than 5 or less than 2 or less than 1. The hydrocarbon-terminated polyether-polyamide block copolymer of formula (1) does not have any free amine groups, and accordingly has an amine number of zero. However, when prepared from diacid, diamine and hydrocarbon-terminated polyether according to a process described herein, some of the diamine may not react with the diacid, and according the final product may have some unreacted amine groups that will be responsible for the product having an amine number greater than zero. Preferably, the product has a minor amount of this unreacted diamine, and thus has only a small amine number. Amidification catalysts may be used to encourage all of the diamine to react with carboxyl groups, so as to minimize the amount of free amine, i.e., to reduce the amine number of the product.

In one aspect, the present invention provides hydrocarbon-terminated polyether-polyamide block copolymers, and compositions containing these copolymers, that has a softening point of 50-150° C. (Ring and Ball, or Mettler). In another aspect, the softening point is 75-125° C., while in another aspect the softening point is 75-100° C., while in another aspect the softening point is 80-120° C.

In one aspect, the present invention provides hydrocarbon-terminated polyether-polyamide block copolymers, and compositions containing these copolymers, that has a weight or number average molecular weight of 2,000 to 30,000. The molecular weight is measured by preparing a solution of the copolymer or composition in a suitable solvent, e.g., tetrahydrofuran (THF) and identifying the retention time of the copolymer by gel permeation chromatography, and comparing that retention time to the retention times of solutions of polystyrene having known molecular weight characterizations. In one aspect, the copolymers have a weight or number average molecular weight of greater than 1,000. In another aspect, the copolymers have a weight average molecular weight of up to 50,000. In other aspects, the copolymers have a weight average molecular weight in the range of 2,000 to 50,000; 5,000 to 50,000; 5,000 to 25,000; and 10,000 to 25,000. The molecular weight can be controlled by controlling the ratio of monofunctional to difunctional reactants. Among other features, the hydrocarbon termination on the polyether reactant allows for control of the molecular weight of the copolymer. If both ends of the polyether reactant were reactive, e.g., the polyether contained hydroxyl functionality at both ends, then the polyether could not be utilized as a terminator in the preparation of copolymers of the present invention.

In one aspect, the present invention provides hydrocarbon-terminated polyether-polyamide block copolymers, and compositions containing these copolymers, that have a viscosity, as measured on the neat copolymer or composition at 160° C., of less than 5,000 centipoise (cPs, or cps), or less than 4,000 cPs, or less than 3,000 cPs, or less than 2,000 cPs, or less than 1,000 cPs Typically, the copolymer and compositions will have a melt viscosity, as measured on the neat copolymer or composition at 160° C., of more than 50 cPs, typically more than 500 cPs.

In one aspect, the present invention provides a hydrocarbon-polyether-polyamide-polyether-hydrocarbon block copolymer of the formula

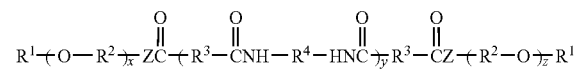

wherein, independently at each occurrence, R$^1$ is a C$_{1-8}$ hydrocarbon radical; R$^2$ is a C$_{2-4}$ hydrocarbon diradical; R$^3$ is a C$_{2-52}$ hydrocarbon diradical, where at least 50% of the R$^3$ diradicals are derived from dimer acid; R$^4$ is selected from C$_{2-8}$ hydrocarbon diradicals and polyether diradicals of the formula —(R$^{11}$—O)$_g$—R$^{11}$— wherein R$^{11}$ is a C$_2$-C$_6$ hydrocarbon diradical independently selected at each occurrence and g is an integer from 2 to 100; Z is selected from O and NH; x is an integer from 2 to 100; y is an integer equal to 1 or more that provides a copolymer molecular weight of 2,000 to 50,000, and z is an integer from 2 to 100. The value of y can be controlled simply by adjusting the ratio of monofunctional to difunctional reactants.

Block copolymers of the present invention may be prepared by reacting together compounds of the formulae R$^1$—(O—R$^2$)$_x$—W, HOOC—R$^3$—COOH, and H$_2$N—R$^4$—NH$_2$, where W represents either an amine, hydroxyl or carboxylic acid group. As used herein an amine group (—NH$_2$), a carboxylic acid group (—COOH) and a hydroxyl group (—OH) include reactive equivalents thereof. For instance, HOOC—$R^3$—COOH includes reactive equivalents, such as monoesters and diesters, i.e., compounds wherein a carboxylic acid is in esterified form.

Compounds of the formula $R^1$—(O—$R^2$)$_x$—W wherein W is hydroxyl are also known as ether-terminated polyalkylene glycols. These compounds are generally well known and may be readily prepared by methodology described in the scientific and patent literature. For example, a monohydric initiator, i.e., a compound of the formula $R^1$—OH is reacted with an alkylene oxide (an $R^2$ group that includes an epoxide group), e.g., ethylene oxide, propylene oxide, etc. to provide a compound of the formula $R^1$—(O—$R^2$)$_x$—OH. These compounds are available from, e.g. Aldrich Chemical (Milwaukee, Wis.).

In one aspect, block copolymers are prepared from compounds of formula $R^1$—(O—$R^2$)$_x$—W wherein W is hydroxyl and $R^2$ is ethylene (—$CH_2CH_2$—). Such compounds of formula $R^1$—(O—$R^2$)$_x$—W may be referred to herein as ethoxylates or alcohol ethoxylates. Ethoxylates may be obtained from many commercial sources (e.g., Dow, Midland Mich.) or may be prepared by reacting alcohols of formula $R^1$—OH with ethylene oxide to give the structure (2) below $$R^1\text{—O—}(CH_2CH_2O)_m\text{—H} \qquad (2)$$

where $R^1$ is a hydrocarbon group as defined previously, and in one aspect $R^1$ is a $C_{6-22}$ alkyl or aralkyl group. Ethoxylates are typically colorless liquids to low melting point pasty solids depending on the chain length (m). Exemplary ethoxylates having various combinations of $R^1$ groups and molecular weight are given in TABLE A (TABLE A—TYPICAL ETHOXYLATES AND THEIR PROPERTIES). In TABLE A, Manuf. is an abbreviation for manufacturer, EO is an abbreviation for ethylene oxide, % EO refers to the weight percent ethylene oxide in the product, EO/OH refers to the molar ratio of ethylene oxide to hydroxyl, HLB refers to the hydrophile lipophile balance, Shell refers to the Shell Chemical division of the Royal Dutch/Shell Group of Companies (@shell.com) where Shell sells alcohol ethoxylates under the NEODOL™ trademark. Also in TABLE A, Condea refers to CONDEA Vista Company (Houston, Tex.; @condea.de) which sells a number of alcohol ethoxylates under their brand names NONFIX™, BIODAC™, LORODAC™, LIALET™, EMULDAC™ and ALFONIC™ where these materials differ by the $R^1$ group, and the number of ethylene oxide groups in the product.

TABLE A

Typical Ethoxylates and Their Properties

| Ethoxylate | Manuf. | $R^1$ | % EO | EO/OH | MW | HLB |
|---|---|---|---|---|---|---|
| NEODOL™ 23-6.5 | Shell | $C_{12-13}$ | 60 | 6.6 | 484 | 12 |
| NEODOL™ 45-13 | Shell | $C_{14-15}$ | 71.8 | 12.9 | 790 | 14.4 |
| NEODOL™ 91-8 | Shell | $C_{9-11}$ | 69.7 | 8.3 | 524 | 13.9 |
| ALFONIC™ 610-3.5 | Condea | $C_{6-10}$ | 50 | 3.1 | 276 | 10 |
| ALFONIC™ 1618-5 | Condea | $C_{16-18}$ | 46 | 5.1 | 469 | 9 |

In another aspect, block copolymers are prepared from compounds of formula $R^1$—(O—$R^2$)$_x$—W wherein W is hydroxyl and $R^2$ is, independently at each occurrence, selected from ethylene (—$CH_2CH_2$—), propylene (—$CH_2$—$CH(CH_3)$—) and n-butylene (—$CH_2$—$CH(CH_2CH_3)$—). Such compounds of formula $R^1$—(O—$R^2$)$_x$—W may be referred to herein as polyalkylene glycol derivatives. Polyalkylene glycol derivatives may be obtained from many commercial sources (e.g., Dow, Midland Mich.; Union Carbide, Danbury, Conn.; Aldrich, Milwaukee, Wis.) or may be prepared by reacting alcohols of formula $R^1$—OH with ethylene oxide and/or propylene oxide to give the structure (3) below:

$$R^1\text{—}[O(CH_2CH_2O)_z(CH_2CH(CH_3)O)_y]\text{—H} \qquad (3)$$

As commercially available, $R^1$ of the polyalkylene glycol derivative is commonly methyl or n-butyl, but $R^1$ can be any hydrocarbon group. Some typical properties of these materials, which are available from, e.g., Union Carbide and Dow, are given in TABLE B (TABLE B—TYPICAL GLYCOL DERIVATIVES AND THEIR PROPERTIES). In TABLE B, MPEG stands for methyl ether poly(ethylene glycol) (i.e., $R^1$ is methyl and the repeating unit is always ethylene so that Y=0), MBPPG stands for monobutyl ether poly(propylene glycol) (i.e., $R^1$ is butyl and the repeating unit is always propylene so that Z=0), and MBPEGCPG stands for monobutyl ether poly(ethylene glycol-co-propylene glycol), 50/50 PPG/PPE (i.e., $R^1$ is butyl and the repeating unit is both ethylene and propylene, so that Z and Y are each equal to or greater than 1).

TABLE B

Typical Polyalkylene Glycol Derivatives and Their Properties

| Glycol | Manuf. | $R^1$ | MW | $T_m$ (° C.) or Visc @ 20° C. (cSt) |
|---|---|---|---|---|
| MPEG 350 | DOW | $CH_3$ | 350 | −8 |
| MPEG 550 | DOW | $CH_3$ | 550 | 20 |
| MPEG 750 | DOW | $CH_3$ | 750 | 30 |
| MPEG 2000 | Aldrich | $CH_3$ | 2000 | 52 |
| MBPPG 340 | Aldrich | $CH_3(CH_2)_3$ | 340 | 20 |
| MBPPG 1000 | Aldrich | $CH_3(CH_2)_3$ | 1000 | 140 |
| MBPPG 2500 | Aldrich | $CH_3(CH_2)_3$ | 2500 | 1,300 |
| MBPEGCPG 1700 | Aldrich | $CH_3(CH_2)_3$ | 1700 | 350 |
| MBPEGCPG 3900 | Aldrich | $CH_3(CH_2)_3$ | 3900 | 3,600 |

In another aspect, block copolymers are prepared from hydrocarbon-terminated polyethers of the formula $R^1$—(O—$R^2$)$_x$—W wherein W is carboxylic acid. These reactants are also known as oxa acids. These compounds are generally well known and may be readily prepared by methodology described in the scientific and patent literature. For example, a monohydric initiator, i.e., a compound of the formula $R^1$—OH, is reacted with an alkylene oxide (an $R^2$ group derived from an epoxide group), e.g., ethylene oxide, propylene oxide, etc., to provide a compound of the formula $R^1$—(O—$R^2$)$_x$—OH. This $R^1$-terminated polyalkylene glycol is then subjected to oxidation conditions to convert the terminal hydroxyl group to a carboxylic acid group. The resultant oxa acids have the structure (4) shown below, when prepared from ethylene oxide:

$$R^1\text{—O—}(CH_2CH_2O)_m\text{—}CH_2\text{—COOH} \qquad (4).$$

Compounds of formula (4) where m=1 or 2 are available from Hoechst (now Aventis), as experimental products. Some properties of these acids are given in TABLE C (TABLE C—TYPICAL OXA ACIDS AND THEIR PROPERTIES). In TABLE C, AN stands for acid number.

TABLE C

Typical Oxa Acids and Their Properties

| Acid | m | MW | Visc @ 20° C. (mP) | AN (mg KOH/g) |
|---|---|---|---|---|
| 3,6-dioxaheptanoic acid | 1 | 134.1 | 35 | 410 |
| 3,6,9-trioxadecanoic acid | 2 | 178.2 | 73 | 310 |

In another aspect, block copolymers are prepared from compounds of formula $R^1$—$(O$—$R^2)_x$—$W$ wherein W is amine and $R^2$ is one or more of ethylene (—$CH_2CH_2$—), propylene (—$CH_2$—$CH(CH_3)$—), and n-butylene (—$CH_2$—$CH(CH_2CH_2)$—), each independently selected at each occurrence. Such compounds of formula $R^1$—$(O$—$R^2)_x$—$W$ may be referred to herein as polyoxyalkyleneamines. These compounds are generally well-known to one of ordinary skill in the art and may be readily prepared by methodology described in the scientific and patent literature. For example, a monohydric initiator, i.e., a compound of the formula $R^1$—$OH$, is reacted with an alkylene oxide (an $R^2$ group is derived from an epoxide-containing group), e.g., ethylene oxide, propylene oxide, etc., to provide a compound of the formula $R^1$—$(O$—$R^2)_x$—$OH$. This $R^1$-terminated polyalkylene glycol is the subjected to reaction conditions to convert the terminal hydroxyl group to a terminal amino group, e.g., ammonia and hydrogen.

As commercially available, polyoxyalkyleneamines (also known as poly(oxyalkylene) monoamines) generally have the structure (5) below:

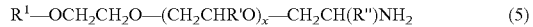

$$R^1\text{—OCH}_2\text{CH}_2\text{O—(CH}_2\text{CHR'O)}_x\text{—CH}_2\text{CH(R'')NH}_2 \quad (5)$$

where $R^1$ is preferably an alkyl group; R' is preferably H, $CH_3$, or $C_2H_5$; and R" is preferably H or $CH_3$. Common commercially-available polyoxyalkyleneamines are typically prepared from ethylene oxide and/or propylene oxide and are available commercially in varying ratios of propylene oxide-to ethylene oxide-based residues. Polyoxyalkyleneamines may be obtained from, e.g., BASF, Mt. Olive, N.J., and Huntsman Chemical, Salt Lake City, Utah. Commercially available polyoxyalkyleneamines and selected properties are given in TABLE D (TABLE D—TYPICAL POLYOXYALKYLENEAMINES AND THEIR PROPERTIES). In TABLE D, both XTJ and JEFFAMINE® are product identifiers used by Huntsman Chemical. In TABLE D, R' is H (when ethylene oxide (EO) is the reactant) or —$CH_3$ (when propylene oxide (PO) is the reactant), where TABLE D provides the PO/EO ratio in the designated polyoxyalkyleneamine.

TABLE D

Typical Polyoxyalkyleneamines and Their Properties

| amine | $R^1$ | R" | PO/EO (mole ratio) | MW | $T_m$ (° C.) |
|---|---|---|---|---|---|
| XTJ-505 | $CH_3$ | $CH_3$ | 9/1 | 600 | −40 |
| XTJ-506 | $CH_3$ | $CH_3$ | 3/19 | 1,000 | 29 |
| XTJ-507 | $CH_3$ | $CH_3$ | 39/6 | 2,000 | −36 |
| XTJ-508(formerly JEFFAMINE ® M-2070 | $CH_3$ | $CH_3$ | 10/32 | 2,000 | 17 |
| XTJ 234 | $CH_3$ | $CH_3$ | 8/49 | 3000 | 36 |
| Diglycol amine | H | H | 0/2 (m = 0) | 105 | |

Thus, the present invention discloses the use of monofunctional polyethers having both hydrocarbon termination and termination selected from amine, hydroxyl and carboxyl, in the preparation of resin compositions comprising a block copolymer of the formula hydrocarbon-polyether-polyamide-polyether-hydrocarbon, where examples of the monofunctional polyether are disclosed above as ethoxylates, polyalkylene glycol derivatives, oxa acids, and polyoxyalkyleneamines.

In addition to the monofunctional polyether, the block copolymers of the present invention are prepared from diamines, where the diamine may be, for example, an alkylene diamine (i.e., a diamine of the formula $H_2N$—$R^4$—$NH_2$ where $R^4$ is a hydrocarbon) or a polyetherdiamine (i.e., a diamine of the formula $H_2N$—$R^4$—$NH_2$ wherein $R^4$ is a polyether, where polyethers are organic moieties having a plurality of ether groups).

Thus, the diamine may be an alkylene diamine having $R^4$ hydrocarbon groups as described herein. Exemplary alkylene diamines, most or all of which are commercially available include, without limitation, ethylenediamine (EDA), 1,2-diaminopropane, 1,3-diaminopropane, 1,4-diaminobutane, 1,2-diamino-2-methylpropane, 1,3-diaminopentane, 1,5-diaminopentane, 2,2-dimethyl-1,3-propanediamine, 1,6-hexanediamine (also known as hexamethylenediamine, HMDA), 2-methyl-1,5-pentanediamine, 1,7-diaminoheptane, 1,8-diaminooctane, 2,5-dimethyl-2,5-hexanediamine, 1,9-diaminononane, 1,10-diaminodecane, 1,12-diaminododecane, diaminophenanthrene (all isomers, including 9,10), 4,4'-methylenebis(cyclohexylamine), 2,7-diaminofluorene, phenylene diamine (1,2; 1,3 and/or 1,4 isomers), adamantane diamine, 2,4,6-trimethyl-1,3-phenylenediamine, 1,3-cyclohexanebis(methylamine), 1,8-diamino-p-menthane, 2,3,5,6-tetramethyl-1,4-phenylenediamine, diaminonaphthalene (all isomers, including 1,5; 1,8; and 2,3) and 4-amino-2,2,6,6-tetramethylpiperidine. In one aspect, the diamine has the formula $H_2N$—$R^{11}$—$NH_2$ wherein $R^{11}$ is a $C_{2-6}$ hydrocarbon diradical.

The diamine may be a polyetherdiamine, also referred to herein as a PAO (for polyalkyleneoxy) diamine. Polyetherdiamines may be obtained from Tomah Products, Inc., Milton, Wis., and Huntsman Chemical. A suitable polyetherdiamine is a poly(propyleneoxy)diamine having the formula $H_2N$—$C(CH_3)HCH_2O$—$(CH_2C(R)HO)_n$—$CH_2C(CH_3)H$—$NH_2$, such as JEFFAMINE® 230 diamine (n is 1-2, and R is $CH_3$), JEFFAMINE® D-400 diamine (n is 4-5 and R is $CH_3$), JEFFAMINE® D-2000 diamine (n is ca. 32 and R is $CH_3$), and XTJ-502 diamine (formerly JEFFAMINE® ED-2003 diamine, n is ca. 41 and R is H), where each of these polyetherdiamines is commercially available from Huntsman Corporation (Salt Lake City, Utah, USA, @huntsman.com). Another suitable diamine is a poly(ethyleneoxy)-co-propyleneoxy) diamine such as HUNTSMAN XTJ-500. Another suitable diamine is DPA-DEG, having CAS Registry No. 271-79-0 and the chemical structure $H_2N$—$CH_2CH_2CH_2$—$O$—$CH_2CH_2$—$O$—$CH_2CH_2$—$O$—$CH_2CH_2CH_2$—$NH_2$. Yet another suitable diamine is XTJ-504 (formerly JEFFAMINE® EDR-148), which is also known as triethyleneglycoldiamine, having CAS Registry No. 929-59-9 and the chemical structure $H_2N$—$CH_2CH_2$—$O$—$CH_2CH_2$—$O$—$CH_2CH_2$—$NH_2$. In one embodiment, the polyetherdiamine has the structure $NH_2CH(CH_3)CH_2O$—$(CH_2CHR'O)_x$—$CH_2CH(CH_3)NH_2$, where R and R' are methyl or H. Huntsman also sells triethyleneglycol diamine under their XTJ-504 diamine designation (formerly JEFFAMINE® EDR-148 diamine) having the structure $H_2N$—$CH_2CH_2$—$O$—$CH_2CH_2$—$O$—$CH_2CH_2$—$NH_2$, which may be used as the polyetherdiamine. Additional suitable polyetherdiamines from Huntsman are XTJ-511 having the structure $H_2N$—$C(CH_3)CH_2$—$O$—

$CH_2CH_2$—O—$CH_2CH_2$—O—$CH_2C(CH_3)H$—$NH_2$; and XTJ-523 diamine having the structure $H_2N$—$C(CH_2CH_3)H$—$CH_2$—$(O$—$C(CH_2CH_3)H$—$CH_2)_a$—$OCH_2C(CH_2CH_3)$—$NH_2$ where a is ca. 26.

In one aspect, the present invention provides a hydrocarbon-polyether-polyamide-polyether-hydrocarbon block copolymer prepared by a process comprising reacting together reactants comprising dimer acid, polyetherdiamine, alkylenediamine, and a monofunctional polyether having both hydrocarbon termination and termination selected from amine, hydroxyl and carboxyl, under reaction conditions that form the block copolymer. Suitable reaction conditions are described herein. In a further aspect, the polyetherdiamine and the monofunctional polyether in total contribute 20-45 wt % of the total weight of the reactants. In a further aspect, the polyetherdiamine has the formula $H_2N$—$(R^{11}$—$O)_g$—$R^{11}$—$NH_2$ wherein $R^{11}$ is a $C_2$-$C_6$ hydrocarbon diradical independently selected at each occurrence, g is an integer from 2 to 50, and the polyetherdiamine contributes 10-30 wt % of the total weight of the reactants. In a further aspect, the monofunctional polyether has the formula $R^1$—$(R^{11}$—$O)_h$—$R^{11}$—$NH_2$ wherein $R^{11}$ is a $C_2$-$C_6$ hydrocarbon diradical independently selected at each occurrence, h is an integer from 2 to 50, and the monofunctional polyether contributes 5-20 wt % of the total weight of the reactants. In a further aspect, the polyetherdiamine has the formula $H_2N$—$(R^{11}$—$O)_g$—$R^{11}$—$NH_2$ wherein $R^{11}$ is a $C_2$-$C_4$ hydrocarbon diradical independently selected at each occurrence from ethylene, propylene and butylene, g is an integer from 2 to 50, and the polyetherdiamine contributes 10-30 wt % of the total weight of the reactants; the monofunctional polyether has the formula $R^1$—$(R^{11}$—$O)_h$—$R^{11}$—$NH_2$ wherein $R^{11}$ is a $C_2$-$C_4$ hydrocarbon diradical independently selected at each occurrence from ethylene, propylene and butylene, h is an integer from 2 to 50, and the monofunctional polyether contributes 5-20 wt % of the total weight of the reactants; and the alkylenediamine has the formula $H_2N$—$R^{11}$—$NH_2$ wherein $R^{11}$ is a $C_2$-$C_6$ hydrocarbon diradical. In a further aspect, dimer acid, polyetherdiamine, alkylenediamine, and monofunctional polyether in total constitute at least 75 wt % of the total weight of the reactants.

Use of a significant level of both polyetherdiamine and polyether-monoamine provides resins having the ability to form clear solutions and/or clear gels in a wide range of polar liquids including dimethylsulfoxide, propylene glycol, ethanol, polypropylene glycol and polyethylene glycol and their monoalkyl ethers. At high weight percentage use levels of terminator (i.e., hydrocarbon-terminated polyether), the resins are extremely soft. As the total level of polyether in the polyamide block decreases, the resin gains the feel and flexibility of a polyamide prepared from ethylene diamine and dimer acid, thus retaining some softness even at low levels of polyether. Some of these resins may dissolve in ethanol, and most demonstrated good solubility in propanol, however gelling behavior was infrequent. In general, propylene glycol is a preferred polar liquid from which to prepare gels containing polar liquid and resins of the invention (i.e., resins prepared from polyetherdiamine and polyethermonoamine). In general, formation of dimer-acid based polyamides, even those including a significant level of both polyether-diamine and polyethermonoamine among the reactants leads to a resin that is not particularly compatible with glycerol.

In one aspect, the "significant level" of polyetherdiamine and polyethermonoamine identified above is in the range of 20-45 wt %, where this range will, for convenience, be referred to herein as the "polyether" content of the resin. In other words, in every 100 grams of resin-forming reactants, there are about 20-45 grams of polyether, where the remaining ca. 80-55 grams are contributed by diacid, preferably dimer acid and/or 1,4-cyclohexanedicarboxylic acid, and may include optional ingredients, where the resin is preferably made with some co-diamine, e.g., ethylene diamine. As a general rule, when the polyether content of the resin is toward the lower part of this range, i.e., the resin has a polyether content of about 20-25 wt %, the resulting resin tends to be relatively better at gelling lower alcohols, e.g., ethanol and propanol. As another general rule, when the polyether content of the resin is toward the upper part of this range, i.e., the resin has a polyether content of about 40-45 wt %, the resulting resin tends to be relatively better for gelling very polar liquids, e.g., dimethylsulfoxide (DMSO) and propylene carbonate. When the polyether content is in the mid-range, i.e., the resin has a polyether content of about 25-40 wt %, or about 25-35 wt %, or about 30-35 wt %, the resulting resin tends to gel the largest number of polar solvents, i.e., the resulting resin is a good gellant for most polar solvents.

The polyether content of the resin is due to the amount of mono-functional polyether and di-functional polyether present in the reactants. As a general rule, increasing the relative amount of mono-functional polyether within the starting materials used to prepare the resin will tend to decrease the average molecular weight of the resulting resin. In one aspect, the polyetherdiamine contributes 10-30 wt % of the total weight of the reactants used to form the block copolymer. A preferred polyetherdiamine has the structure $H_2N$—$(R^{11}$—$O)_g$—$R^{11}$—$NH_2$ wherein $R^{11}$ is a $C_{2-6}$ hydrocarbon diradical (i.e., a diradical having 2, 3, 4, 5, or 6 carbons and hydrogens as needed to fill all open valence sites of the carbons, but no other atoms, also referred to as $C_2$-$C_6$ hydrocarbon diradical) independently selected at each occurrence, and g is an integer from 2 to 50. A preferred polyetherdiamine has the structure of JEFFAMINE® D-400 diamine. Additionally, or in an independent aspect, the monofunctional polyether may contribute 5-20 wt % of the total weight of the reactants. A preferred monofunctional polyether has the formula $R^1$—O—$(R^{11}$—$O)_h$—$R^{11}$—$NH_2$ wherein $R^1$ is a $C_{1-6}$ hydrocarbon radical and $R^{11}$ is a $C_{2-6}$ hydrocarbon diradical independently selected at each occurrence, and h is an integer from 2 to 50. A preferred monofunctional polyether has the structure of JEFFAMINE® M-2070 monoamine.

When a polyetherdiamine and polyethermonoamine-derived resin is dissolved in a polar liquid, and then this solution is diluted with water, it is typically observed that the solution remains homogeneous, i.e., the resin does not precipitate. Frequently, upon dilution with water, the resin/polar liquid/water mixture takes on a bluish cast, indicating the presence of a microemulsion form.

In preparing the resins of the present invention, the diamine may be a mixture of hydrocarbon diamine and polyetherdiamine. In addition, it is generally observed that increasing the level of termination, i.e., increasing the relative amount of monoreactive hydrocarbon-terminated polyether, tends to provide a resin with a relatively lower softening point and melt viscosity. The use of hexamethylene diamine (HMDA), in lieu of some or all of ethylene diamine (EDA), tends to lower the softening point of the resin. In one aspect of the invention, ethylene diamine is a reactant used in preparing the block copolymer, and in particular is used in preparing the polyamide block of the block copolymer. Typically, EDA is blended with a polyetherdiamine, in order to prepare the polyamide block of the block copolymer of the present invention, where the diamine(s) are reacted with diacid, e.g., dimer acid.

The inclusion of co-diacid, i.e., diacid other than dimer acid, e.g., sebacic acid, in the reaction mixture tends to raise the softening point of the resulting resin. The polyethermonoamine should not contain any hydroxyl groups. The inclusion of hydroxyl groups is detrimental to the gelling ability of the resin made from the monoamine. Accordingly, hydroxyl terminated polyethers are not included within the polyethermonoamine reactants of the present invention. Indeed, in one aspect of the invention, no hydroxyl-containing materials, e.g., alcohols (compounds containing one hydroxyl group) or polyols (compounds containing two or more hydroxyl groups), are used as a reactant to prepare a resin of the present invention. In one aspect, no polyol is included among the reactants to prepare a block copolymer of the invention. In other aspects, if hydroxyl-containing materials are included as a reactant(s), then the hydroxyl-containing materials contribute less than 5 wt %, or less than 3 wt %, of the total weight of the reactants.

Some of the inventive resins, particularly those prepared from polyetherdiamines and polyether hydrocarbon-terminated monoamines, have the unusual ability to form microemulsions in mixtures of water and a polar liquid. These blends are clear and homogeneous but have a distinct blue cast and can be either immobile gels or fluid liquids, depending on the concentration of the resin and the polar liquid. They can be diluted with water without formation of a precipitate. Block copolymers of the present invention that form such microemulsions may be particularly useful as corrosion inhibitors in aqueous systems.

As described herein, diamines, dicarboxylic acids, and hydrocarbon-terminated polyethers having a reactive group W selected from hydroxyl, amine and carboxyl are preferred starting materials to form the triblock copolymers of the invention. These starting materials are preferably reacted together with a stoichiometry, and under reaction conditions, such that the acid number of the resulting block copolymer is less than 25, preferably less than 15, and more preferably less than 10, while the amine number is preferably less than 10, more preferably less than 5, and still more preferably less than 1. The softening point of the block copolymer is preferably greater than room temperature, more preferably is about 50° C. to about 150° C., and still more preferably is about 75° C. to about 125° C.

It is important to control the stoichiometry of the reactants in order to prepare a block copolymer according to the invention. The following discussion regarding reactant stoichiometry uses the terms "equivalent(s)" and "equivalent percent", where these terms are intended to have their standard meanings as employed in the art. However, for additional clarity, it is noted that equivalents refer to the number of reactive groups present in a molar quantity of a molecule, such that a mole of a dicarboxylic acid (e.g., sebacic acid) has two equivalents of carboxylic acid, while a mole of monoamine has one equivalent of amine. Furthermore, it is emphasized that in preparing a triblock copolymer of the invention, the diacid has only two reactive groups (both carboxylic acids, although dimer acid may contain a small amount of tricarboxylic acid), the diamine has only two reactive groups (both primary amines) and the hydrocarbon terminated polyether reactant has a single reactive group selected from amine, hydroxyl and carboxyl. Furthermore, these are preferably, although not necessarily, the only reactive materials present in the reaction mixture.

When co-diacid is employed to prepare a block copolymer, the co-diacid preferably contributes no more than about 50% of the equivalents of carboxylic acid present in the reaction mixture. Stated another way, the co-diacid contributes from 0-50 equivalent percent of the acid equivalents in the reaction mixture. Preferably, the co-diacid contributes 0-30 equivalent percent, and more preferably contributes 0-10 equivalent percent of the acid equivalents in the reaction mixture.

The stoichiometry of the reactants will have a significant impact on the composition of the block copolymer. For example, triblock copolymers made with increasing amounts of polyether will tend to have lower (number and weight) average molecular weights. On the other hand, as less polyether is used, the average molecular weight of the molecules that comprise the block copolymer will increase. In general, increasing the average molecular weight of the copolymer will tend to increase the melting point and melt viscosity of the copolymer. When a high melting point copolymer is combined with a polar liquid to thereby form a gel, the gel will tend to have a firmer consistency than does a gel formed from a copolymer with a low melting point.

In order to prepare a block copolymer of the present invention, the above-described reactants (diacid, diamine and polyether, or reactive equivalents thereof) may be combined in any order. In one embodiment of the invention, the reactants are simply mixed together and heated for a time and at a temperature sufficient to achieve essentially complete reaction, to thereby form the block copolymer. In another embodiment, the diacid and diamine are reacted together, followed by addition of the monoreactive polyether. During formation of the block copolymer, the diacid and diamine compounds will alternate to form what may be termed an alternating copolymer, i.e., the polyamide block of the block copolymer is an alternating copolymer of diacid and diamine. The terms "complete reaction" and "reaction equilibrium" as used herein have essentially the same meaning, which is that further heating of the product does not result in any appreciable change in the acid or amine numbers of the copolymer.

Thus, the block copolymer may be formed in a one-step procedure, wherein all of the diacid (including co-diacid), diamine (preferably including ethylene diamine) and polyether are combined and then heated to about 180-250° C. for a few hours, typically 2-8 hours. When lower temperatures are used, a longer reaction time is typically needed to achieve complete reaction. When the reaction temperature is too high, the reactants and/or products may undergo undesirable thermally-induced decomposition. Typically, the reactants must be exposed to a temperature in excess of 100° C. in order to drive off the water formed by the condensation of the reactants. Since one or more of the reactants may be a solid at room temperature, it may be convenient to combine each of the ingredients at a slightly elevated temperature, and then form a homogeneous mixture prior to heating the reaction mixture to a temperature sufficient to cause reaction between the diacid, diamine and polyether. Alternatively, although less preferably, two of the reactants may be combined and reacted together, and then the third reactant is added followed by further heating until the desired product is obtained. Reaction progress may be conveniently monitored by periodically measuring the acid and/or amine number of the product mixture.

As one example, dimer acid may be reacted with diamine so as to form polyamide, and then this intermediate polyamide may be reacted with polyether to form a hydrocarbon terminated polyether-polyamide-polyether block copolymer. Because the components of the block copolymer are preferably in reaction equilibrium (due to transamidation and/or transesterification reactions), the order in which the reactants are combined typically does not impact on the properties of the product copolymer.

Any catalyst that may accelerate amide and/or ester formation between carboxyl, amine and/or hydroxyl groups may be present in the reaction mixture described above. Thus, mineral acid such as phosphoric acid, or tin compounds such as dibutyltin oxide, may be present during the reaction. In addition, it is preferred to remove water from the reaction mixture as it is formed upon amide and, optionally, ester formation. This is preferably accomplished by maintaining a vacuum on the reacting mixture, or by passing a stream of an inert gas (e.g., nitrogen) across the top of the reaction mixture.

The block copolymers of the invention may be used to thicken and/or gel a liquid (where the term "a liquid" includes a mixture of liquids). As used herein, the term liquid refers to any substance that is or can be a liquid (as opposed to a solid or gas) at a temperature between 10-60° C. Generally stated, a liquid is a fluid material where the components of the material are held together by intermolecular interactions, as opposed to a gas, where a gas is also fluid but the components of the gas are not held together by intermolecular interactions. A material is a "liquid" according to the present invention even though under a specific set of conditions the material does not flow. For instance, methyl ethyl ketone (MEK), also known as 2-butanone, is a liquid according to the present invention even though MEK can be a solid under certain conditions (e.g., at less than −87° C.) and can be a gas under other conditions (e.g., at greater than 80° C.). Thus, a composition of the present invention that includes a "liquid" does not necessarily have that liquid in a fluid liquid state. For instance, a composition of the present invention that contains MEK is still a composition of the present invention even though the composition may be at such a low temperature that the liquid no longer flows, and in fact may be regarded as a solid. So long as the candidate liquid in neat form would flow at a temperature between 10-60° C., then that is a liquid according to the present invention.

The composition of the present invention may be a liquid, which will typically be the case at elevated temperatures. The composition may alternatively be a gel, which will typically be the case at room temperature. Even when the composition is in the gel state, as explained above, the polar liquid of the composition will be deemed to be a "liquid", i.e., a fluid, so long as the polar liquid in a neat state would be a fluid liquid at least one temperature in the range of 10-60° C. The polar liquid need not be fluid in the composition of the invention, e.g., the composition need not, and preferably does not demonstrate syneresis.

The liquid present in the compositions of the present invention is not only fluid at least one temperature in the range of 10-60° C., but it is also polar. The term polar means that the liquid contains a dipole moment. In one aspect, the liquid contains a heteroatom, e.g., oxygen or nitrogen, in addition to one or more carbons, where the presence of the heteroatom will typically imbue the liquid with a dipole so that the liquid is a polar liquid according to the present invention. For instance, the polar liquid may contain one or more oxygen atoms, and be a ketone-containing liquid, an ester-containing liquid or an ether-containing polar liquid. The polar liquid may contain oxygen and nitrogen atoms, e.g., the polar liquid may be an amide-containing liquid. The polar liquid may contain oxygen and sulfur atoms, e.g., the polar liquid may be a sulfoxide-containing liquid.

In a preferred embodiment, the polar liquid or surfactant forms a gel upon being combined with a block copolymer of the present invention. As used herein, the term "a", as in the term "a polar liquid" refers to one or more of the indicated items. For example, "a fragrance" refers to one or more fragrance chemicals.

In one aspect, the polar liquid is an ester-containing liquid having a formula selected from $R^6$—$CO_2$—$R^6$ and $R^6$—$CO_2$—$R^7$—$CO_2$—$R^6$ wherein $R^6$ and $R^7$ are organic moieties having 1-12 carbons, where two $R^6$ moieties in a liquid may be joined together to provide a lactone, and a $R^6$ and $R^7$ moiety in a liquid may be joined together to form a lactone. For example, $R^6$ may be selected from $C_1$-$C_{12}$ alkyl, $C_1$-$C_{12}$ hydroxy-substituted alkyl, $C_1$-$C_{12}$ alkoxy-substituted $C_1$-$C_{12}$ alkyl, $C_6$-$C_{12}$ aryl-substituted $C_1$-$C_{12}$ alkyl, $C_1$-$C_{12}$ alkenyl, $C_1$-$C_{12}$ hydroxyalkenyl, $C_1$-$C_{12}$ alkoxy-substituted $C_1$-$C_{12}$ alkenyl, $C_8$-$C_{12}$ aryl, $C_1$-$C_{12}$ alkyl-substituted $C_6$-$C_{12}$ aryl, $C_6$-$C_{12}$ hydroxy-substituted aryl, $C_6$-$C_{12}$ alkoxy-substituted $C_6$-$C_{12}$ aryl; and $R^7$ may be selected from $C_1$-$C_{12}$ alkylene, $C_1$-$C_{12}$ hydroxy-substituted alkylene, $C_2$-$C_{12}$ alkenylene, $C_6$-$C_{12}$ arylene, $C_6$-$C_{12}$ hydroxy-substituted arylene, $C_1$-$C_{12}$ alkoxy-substituted $C_6$-$C_{12}$ arylene. As another example, the ester-containing liquid may be selected from the group consisting of ethyl lactate, butyl propionate, dibutyl adipate, ethoxyethyl propionate, butyl acrylate, vinyl propionate, butyl acetate, dibutyl sebacate, diethylphthalate, vinyl acetate, methyl methacrylate, ethyl acetate, ethyl hexyl acetate, and gamma-butyrolactone.

In another aspect, the polar liquid is an aromatic liquid. For example, the aromatic liquid may be selected from the group consisting of benzene, toluene, o-xylene, m-xylene, p-xylene, styrene, alpha-methyl styrene, ($C_1$-$C_{18}$alkyl)-benzoate, ($C_1$-$C_{18}$ alkyl)salicylate, and ($C_1$-$C_{12}$ alkyl)($C_1$-$C_{12}$ alkyl)phthalate.

In another aspect, the polar liquid is a polar aprotic liquid. For example, the polar aprotic liquid may be selected from the group consisting of N-methylpyrrolidinone, propylene carbonate, tetrahydrofuran, dimethyl sulfoxide, methylene chloride, and dichloroethane.

In another aspect, the polar liquid is a ketone-containing liquid. For example, the ketone-containing liquid may have the formula $R^6$—$C(=O)$—$R^6$ wherein $R^6$ at each occurrence is independently selected from organic moieties having 1-12 carbons, where two $R^6$ moieties in a liquid may be joined together to provide a cyclic ketone. For further example, the ketone-containing polar liquid may be selected from acetone, methyl ethyl ketone, methyl isobutyl ketone and cyclohexanone.

In another aspect, the polar liquid is a sulfoxide-containing liquid. For example, the sulfoxide-containing liquid may have the formula $R^8$—$S(=O)$—$R^8$ and $R^8$ is independently selected at each occurrence from $C_1$-$C_6$ alkyl.

In another aspect, the polar liquid is a glycol ether. For example, the polar liquid may be a glycol ether of the formula $R^9$—[O—$R^{10}$—$]_n$—OH wherein $R^9$ is a $C_1$-$C_{22}$ hydrocarbon, $R^{10}$ is a $C_2$-$C_6$ hydrocarbon independently selected at each occurrence, and n is an integer selected from 1, 2, 3, 4, 5 and 6. As another example, the glycol ether may be ethyleneglycol mono phenyl ether, dipropyleneglycol mono methyl ether or tripropyleneglycol mono methyl ether.

Polar liquids are very well known in the art, and can be obtained from many commercial suppliers. See, e.g., Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co.

Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hannover, Germany), Spectrum Quality Product, Inc. (New Brunswick, N.J.), TCI America (Portland Oreg.), Trans World Chemicals, Inc. (Rockville Md.), and Wako Chemicals USA, Inc. (Richmond Va.).

In another aspect, the polar liquid may include, or may exclusively be, a liquid fragrance. Liquid fragrances are well known in the art and are sold by many companies. Liquid fragrances are also known as aroma chemicals. For example, the following companies sell fragrance materials as a major part of their business: IFF (New York, N.Y., USA; see iff. com); Givaudan (Vernier, Switzerland; see givaudan.com); Firmenich (Princeton, N.J., USA; see firmenich.com); Quest International (Naarden, The Netherlands; see quest-international.com); Takasago (Rockleigh, N.J., USA; see takasago-i.co.jp); Haarman & Reimer (Holzminden, Lower Saxony, Germany; see haarmann-reimer.com); Dragoco (Holzminden, Lower Saxony, Germany; see dragoco.com); T. Hasegawa Co., Ltd. (Tokyo, Japan; see t-hasegawa.co.jp); Mane SA (Bar-sur-Loup, France; see mane.com); Aldrich-Sigma Flavors and Fragrances, a group within Aldrich Chemical Co., Inc. (Milwaukee, Wis., USA: see sigma-aldrich.com/safc).

Fragrance chemicals may be classified based upon their common functional groups. For examples, acetylenes, alcohols, aldehydes, amines, amino acids, carboxylic acids, essential oils, ester/lactones, ethers/acetals, heterocycles, hydrocarbons, ketones, nitrites, olefins (including cumulated double bonds), and sulfur compounds (sulfides, disulfides and mercaptans) are classes of fragrance chemicals. Fragrance chemicals may also be classified based on their common smell. For example, aliaceous, animal, balsamic, camphoraceous, citrus, coffee, earthy, ethereal, floral, fruity, green, herbaceous, meaty, medicinal, minty, mossy, musty, nutty, pepper, smoky, soapy, spicy, sulfurous, vegetable, waxy, wine-like and woody are some common smells that are recognized by the aroma chemist. These classes of fragrance chemicals represent fragrance chemicals according to the present invention. Essential oils, which are naturally-derived fragrance chemicals, are also liquid fragrances according to the present invention.

The combination of a resin composition comprising a block copolymer of the formula hydrocarbon-polyether-polyamide-polyether-hydrocarbon, and a liquid fragrance chemical, can be utilized as a fragrance-emitting article. Fragrance-emitting articles are well known as a desirable material of commerce. In order to formulate a fragrance-emitting article from a resin composition comprising a block copolymer of the formula hydrocarbon-polyether-polyamide-polyether-hydrocarbon according to the present invention, blends of liquid fragrance and resin may be prepared at various weight ratios, e.g., 10%, 20%, 30%, 40%, 50%, 60%, 70%, 80%, and 90% by weight of liquid fragrance in a combination of liquid fragrance and resin. These blends may be heated to provide a homogeneous composition, and then cooled to provide the fragrance-emitting article. The formulator will be able to select from these formulations a suitable formulation that meets the needs of consistency and fragrance-release characteristics for the desired end-use. When gel-like consistencies are created, the gel may be molded into various shapes. Other components may be added to the compositions, to provide desirable end-use properties in addition to fragrance release.

In another aspect, the polar liquid may include, or may exclusively be, a liquid polyepoxy resin. Although liquid polyepoxy resins are well known in the art, some salient features of liquid polyepoxy resins will be described. In general, liquid polyepoxy resins are any liquid organic compound having at least two oxirane rings, where oxirane rings are also known as epoxy groups. In addition to the epoxy groups, the polyepoxy resin will contain aliphatic, alicyclic, heterocyclic, cycloaliphatic, and/or aromatic groups, in addition to combinations thereof. The polyepoxides may be linear polymers having terminal epoxy groups (for example, a diglycidyl ether of a polyoxyalkylene glycol), polymers having skeletal oxirane units (for example, polybutadiene polyepoxide), or polymers having pendent epoxy groups (for example, a glycidyl methacrylate polymer or copolymer). The molecular weight of the liquid polyepoxy resin may vary from about $10^2$ to about $10^5$ or more. Mixtures of various epoxy resins can also be used in the hot melt compositions of the invention.

Liquid polyepoxy resins are frequently described in the patent, journal and trade literature. See, e.g., U.S. Pat. No. 3,117,099 and U.S. Pat. No. 3,018,262. Specific exemplary polyepoxy resins include halogenated epoxy resins, 1,4-butanediol diglycidyl ether (for example, ARALDITE RD-2™ from Ciba-Geigy Corp.), diglycidyl ethers of Bisphenol A (for example, EPON 828™, EPON 1004™, and EPON 1001F™ from Resolution Performance Products, Inc. (Houston, Tex., formerly the Resins & Versatics business of Shell Chemicals); and DER-332™ and DER-334™ from Dow Chemical Co., Midland, Mich.), diglycidyl ether of Bisphenol F (for example, ARALDITE GY281™ from Ciba-Geigy Corp., Hawthorne, N.Y., and EPON 862™ from Resoultion Performance Products, Inc.), 3,4-epoxycyclohexyl-methyl-3,4-epoxycyclohexene carboxylate (for example, ERL-4221 ™ from Dow Chemical Company), vinylcyclohexene dioxide (for example, ERL 4206™ from Dow Chemical Co.), bis(3,4-epoxycyclohexyl) adipate (for example, ERL-4299™ from Dow Chemical Co), dipentene dioxide (for example, ERL-4269™ from Dow Chemical Company), epoxidized polybutadiene (for example, OXIRON 2001 ™ from FMC Corp.), 2-(3,4-epoxycyclohexyl-5,5-spiro-3,4-epoxy) cyclohexanemetadioxane (for example, ERL-4234™ from Dow Chemical Company), epoxy silanes, for example, beta-3,4-epoxycyclohexyl-ethyltrimethoxysilane and gamma-glycidoxypropyltrimethoxysilane, hydrogenated bisphenol A-epichlorohydrin based epoxy resins (for example EPONEX 1510™ from Resolution Performance Products, Inc.), and polyglycidyl ethers of phenol-formaldehyde novolaks (for example, DEN-431™ and DEN-438™ from Dow Chemical Co.).

The combination of a resin composition comprising a block copolymer of the formula hydrocarbon-polyether-polyamide-polyether-hydrocarbon, and a liquid polyepoxy resin, can be utilized in, e.g., preparing structural materials. Polyepoxides can be cured by various materials well known in the art, e.g., amines, to form a crosslinked structure. This crosslinking structure can take may shapes, e.g., a film. The film may be used as a top coat for a coated substrate, where the film provides effective barrier properties that allows the coated substrate to retain desirable properties for longer periods of time. Cured epoxy resin may also be used as an adhesive composition. The addition of the resin composition comprising a block copolymer of the formula hydrocarbon-polyether-polyamide-polyether-hydrocarbon with the polyepoxy resin according to the present invention does not preclude the polyepoxy resin from being utilized in those applications to which the polyepoxy resin would be used in the absence of the resin composition comprising a block copolymer of the formula hydrocarbon-polyether-polyamide-polyether-hydrocarbon.

In order to determine a proper formulation of resin composition comprising a block copolymer of the formula hydrocarbon-polyether-polyamide-polyether-hydrocarbon and liquid epoxy resin, the two components may be combined in various weight ratios. For example, blends of liquid polyepoxy resin and block copolymer-containing composition may be prepared at various weight ratios, e.g., 5%, 10%, 20%, 30%, 40%, 50%, 60%, 70%, 80%, and 90% by weight of liquid polyepoxy resin in a combination of polyepoxy resin and block copolymer-containing resin. These blends may be heated to provide a homogeneous composition, and then cooled to room temperature. The formulator will be able to select from these formulations a suitable formulation that meets the needs of consistency and reactivity with curing agents, for the desired end-use. When gel-like consistencies are created, the gel may be molded into various shapes. Other components may be added to the compositions, to provide desirable end-use properties in addition to structural and adhesive properties.

In another aspect, the resin composition as described herein may be combined with a surfactant, preferably a liquid surfactant. The term "surfactant" includes soaps and detergents. Surfactants are a very well known class of material, and they need not be defined herein. Many of the above-listed suppliers of commercial chemicals will also sell surfactants. However, it will be noted that many surfactants may be classified based on their ionic nature, that is, into the classes of anionic, cationic, zwiterionic, and non-ionic. Each of these surfactant types may be included within a composition according to the present invention.

Exemplary nonioinic surfactants that may be used in the compositions of the present invention include, without limitation, surfactants containing an ester bond, such as glycol esters of fatty acids, glycerol esters of fatty acids, polyglycerol esters of fatty acids, tetritol, pentitol and hexitol esters of fatty acids, polyethylene glycol esters of fatty acids, sucrose esters of fatty acids, sucrose esters of triglycerides, sorbitan esters of fatty acids and polyoxy-ethylenated sorbitan esters or polysorbates. The nonionic surfactant may contain an ether bond, such as polyoxyethylene glycol alkylphenyl ethers and polyoxyethylene glycol fatty alkyl ethers. The nonionic surfactant may contain an amide bond, e.g., polyoxyethylenated alkylamides and alkylene oxide copolymers. Of the various classes of surfactants, nonionics are a preferred surfactant for incorporation into the compositions of the present invention because many nonionics are liquid, while cationic and anionic tend to be solids.

Exemplary cationic or zwitterionic surfactants include betaines such as decyl betaine, lauryl betaine, lauramidopropyl betaine, myristyl betaine, myristamidopropyl betaine, coco-betaine, cocoamidoethyl betaine, cocoamido-propyl betaine, cetyl betaine, palmamidopropyl betaine, palmitamidopropyl betaine, ricinoleamidopropyl betaine, stearamidopropyl betaine, stearyl betaine, oleyl betaine, oleamidopropyl betaine, and behenyl betaine. Another cationic or zwitterionic surfactant class is the sultaines, where exemplary sultaineds are lauryl sultaine, lauryl hydroxysultaine, coco-sultaine, coco-hydroxysultaine, cocoamido-propyl hydroxysultaine and oleamidopropyl hydroxysultaine. Alkyltrimethyl-ammonium salts are an exemplary cationic type of surfactant, where representative examples include dodecyltrimethylammonium bromide or chloride, cocotrimethylammonium chloride, cetyltrimethylammonium chloride, bromide, methosulphate or tosylate, (hydrogenated) trimethylammonium tallow chloride, stearyltrimethylammonium chloride, octyldodecyltrimethylammonium chloride, behenyltrimethylammonium chloride or methosulphate or benzalkonium chloride, bromide or saccharinate, cetalkonium chloride, cetearalkonium bromide, lauralkonium chloride or bromide, stearalkonium chloride, olealkonium chloride, behenalkonium chloride and cocoylbenzylhydroxyethylimidazolinium chloride.

Exemplary anionic surfactants include materials known as soaps, and include carboxylate and sulfonate salts, e.g., fatty acid salts including sodium or potassium or other suitable counterion.

In order to determine a proper formulation of resin composition comprising a block copolymer of the formula hydrocarbon-polyether-polyamide-polyether-hydrocarbon and surfactant, the two components may be combined in various weight ratios. For example, blends of surfactant and block copolymer-containing composition may be prepared at various weight ratios, e.g., 5%, 10%, 20%, 30%, 40%, 50%, 60%, 70%, 80%, and 90% by weight of surfactant in a combination of surfactant and block copolymer-containing resin. These blends may be heated to provide a homogeneous composition, and then cooled to room temperature. The formulator will be able to select from these formulations a suitable formulation that meets the needs of consistency and surfactancy. When gel-like consistencies are created, the gel may be molded into various shapes. Other components may be added to the compositions, to provide desirable end-use properties in addition to surfactancy properties. These compositions may be used in, for example, cosmetics and cleaning compositions.

The block copolymer and polar liquid may be combined so as to provide a mixture that has a gel-like consistency. In general, materials that have a gel-like character will maintain their shape when undisturbed but flow upon being rubbed. Gels prepared with block copolymers of the present invention may be anywhere from soft to hard, where a "hard" gel has a rigid structure and is very resistant to deformation, while a "soft" gel exhibits some, but not too much, resistance to deformation. An illustration of "soft" gel may be seen in the preparation of Jell-O® dessert, which is a well known food product from Kraft Foods Inc. (division of Philip Morris Companies Inc., Northfield, Ill.). When prepared according to the package instructions, Jell-O® dessert is mixed with water to form a relatively soft gel. A gellant may be distinguished from a Theological additive, where a Theological additive increases the shear thinning of a polar liquid/additive combination, while a gellant imparts a solid phase to the polar liquid/gellant combination. In one aspect of the invention, the block copolymer of the present invention is not a rheological additive. In one aspect, the present invention provides a gel comprising the block copolymer of the present invention and a suitable polar liquid.

The polar liquid is a liquid at room temperature or slightly above room temperature. A preferred polar liquid is a polar solvent, where exemplary polar solvents include lower alcohols (e.g., methanol, ethanol, propanol, butanol), glycols, ethers, glycol ethers (i.e., polyalkyleneglycol ethers), and polyols. The polar solvent may be a mixture of solvents. Exemplary polar solvents are described in TABLE E (TABLE E—POLAR LIQUIDS CONTAINING HYDROXYL AND/OR ETHER FUNCTIONALITIES). DOWANOL™ E-200 and E-300 are two exemplary polyethylene glycols from the DOWANOL™ family of glycol ethers from Dow (Midland, Mich.; @dow.com) while DESMOPHEN™ 550 U and 1600

U are polyether polyols from the DESMOPHEN™ family of products from Bayer Corporation (Pittsburgh, Pa.; @bayer.com).

TABLE E

Polar Liquids Containing Hydroxyl and/or Ether Functionalities

| Name | CAS | Structure | Functionality |
|---|---|---|---|
| Hexylene glycol (a.k.a. 2-methyl-2,4-pentandiol) | 107-41-5 | $CH_3CH(OH)CH_2C(CH_3)_2OH$ | 1 secondary OH<br>1 tertiary OH |
| Propylene glycol (a.k.a. 1,2-propanediol) | 57-55-6 | $CH_3CH(OH)CH_2OH$ | 1 primary OH<br>1 secondary OH |
| Ethylene glycol | 107-21-1 | $HOCH_2CH_2OH$ | 2 primary OH |
| Di(propylene glycol) Mixture of 1,2 and 1,3 isomers | 25265-71-8 | $HOC_3H_6OC_3H_6OH$ | 2 primary OH's<br>2 secondary OH's<br>1/1 prim/sec OH<br>1 ether |
| Di(ethylene glycol) ethyl ether | 111-90-0 | $C_2H_5OCH_2CH_2OCH_2CH_2OH$ | 2 ether<br>1 prim. OH |
| Diethylene glycol dimethyl ether (a.k.a. 2-methoxyethyl ether) | 111-96-6 | $CH_3OCH_2CH_2OCH_2CH_2OCH_3$ | 3 ether |
| DOWANOL™ E-200 Poly(ethylene glycol) MW = 200 | 25322-68-3 | $H(OCH_2CH_2)_nOH$ | 2 prim. OH<br>~4 ether |
| DOWANOL™ E-300 Poly(ethylene glycol) MW = 300 | 25322-68-3 | $H(OCH_2CH_2)_nOH$ | 2 prim. OH<br>~6 ether |
| DESMOPHEN™ 1600 U Linear polyether polyol | 25322-69-4 | NOT KNOWN | NOT KNOWN |
| DESMOPHEN™ 550 U Branched polyether polyol | 25723-16-4 | NOT KNOWN | NOT KNOWN |
| Poly(ethylene glycol) dimethyl ether MW = 250 | 24991-55-7 | $CH_3(OCH_2CH_2)_nOCH_3$ | ~6 ether |

In one aspect, the polar liquid is a liquid that contains ether and/or hydroxyl groups. In one aspect of the invention, the polar liquid is DMSO, i.e., dimethylsulfoxide. The liquid may contain more than one component, e.g., ether as well as hydroxyl-containing material. In the mixture, the gellant (block copolymer) typically contributes 10-95%, and the polar liquid typically contributes 5-90%, of the combined weight of the gellant and the polar liquid. Preferably, the gellant is combined with the polar liquid such that the weight percent of gellant in the gellant+polar liquid mixture is about 5-50%, and preferably is about 10-45%. Such mixtures are preferably gels, where the gels may be transparent, translucent or opaque, depending on the precise identities of the gellant and polar liquid, as well as the concentration of gellant in the mixture.

In order to prepare a gel from a polar liquid and block copolymer, the two components are mixed together and heated until homogeneous. A temperature within the range of about 80-150° C. is typically sufficient to allow the block copolymer to completely dissolve in the polar liquid. A lower temperature may be used if a solution can be prepared at the lower temperature. Upon cooling, the mixture forms the gelled composition of the invention. Optional components may be added to the molten composition, and are dispersed and/or dissolved to provide a homogeneous composition prior to cooling of the molten composition.

In another embodiment, the block copolymer-containing gels of the present invention may be formulated such that they are transparent. There are various degrees of transparency, ranging from "crystal" clear to hazy, which may be achieved with gels of the invention. In order to provide some measure of the absolute transparency of a gel, the following test has been devised. A white light is shined through a gel sample of a given thickness at room temperature, and the diffuse transmittance and the total transmittance of the light are determined. The percent haze for a sample is determined by the equation: % haze=(diffuse transmittance/total transmittance)×100. Samples are prepared by melting the gel (or product made therefrom) and pouring the melt into 50 mm diameter molds. The samples may be prepared at two thicknesses, e.g., 5.5±0.4 mm and 2.3±0.2 mm.

Clarity measurements may be made on a Hunter Lab Ultrascan Sphere Spectrocolorimeter using the following settings: specular included, UV off, large area of view, illuminate D65, and observer 10°. Using this protocol with a 2.3 mm thickness sample, block copolymer-containing gel of the present invention may have a % haze value of less than 75, while paraffin wax has a % haze value of over 90. The % haze value for a gel of the present invention can be increased if desired, by appropriate selection of polar liquid and gellant. Thus, the present invention provides gels (and articles made therefrom) having a transparency (measured by % haze) of less than 75, preferably less than 50, more preferably less than 25, still more preferably less than 10, and yet still more preferably of 5 or less.

In one embodiment, the gels containing block copolymer of the present invention are also stable, in that they do not display syneresis. As defined in the McGraw-Hill Dictionary of Scientific and Technical Terms (3$^{rd}$ Edition), syneresis is the spontaneous separation of a liquid from a gel or colloidal suspension due to contraction of the gel. Typically, syneresis is observed as the separation of liquid from a gel, and is sometimes referred to as "bleeding", in that wetness is seen along the surfaces of a gel that displays syneresis. From a commercial point of view, syneresis is typically an undesirable property, and the gels of the present invention desirably, and surprisingly do not exhibit syneresis. In one embodiment, the gels of the invention, and articles prepared therefrom, may be stable in the sense that they do not exhibit syneresis. Thus, they do not have an oily feeling when handled.

A gel formed from a block copolymer and the present invention may be used to prepare an antiperspirant or deodorant. The antiperspirant may also contain one or more of aluminum chlorohydrate, aluminum-zirconium tetrachlorohydrate, aluminum-zirconium polychlorohydrate complexed with glycine, and aluminum-zirconium complexed with any of trichlorohydrate, octachlorohydrate, and sesquichlorohydrate. The gels, and the formulated antiperspirant, are preferably transparent.

The block copolymer-containing gels of the invention may be (although need not be) essentially transparent. When transparent, the gels may be combined with colorants (as well as other ingredients) to form lipstick or other cosmetic products, without the gel interfering with or tainting the appearance of the colorant. The gels of the present invention may be combined with aluminum zirconium salts, as well as other ingredients, to form colorless underarm deodorant/antiperspirant, which is currently quite popular. The gels of the invention are also useful in other personal care products, e.g., cosmetics such as eye make-up, lipstick, foundation make-up, costume make-up, as well as baby oil, make-up removers, bath oil, skin moisturizers, sun care products, lip balm, waterless hand cleaner, medicated ointments, ethnic hair care products, perfume, cologne, oral care bases (e.g., for toothpaste) and suppositories.

In addition, the gels of the present invention may be used in household products such as air fresheners, decorative tabletop food warmers (i.e., they may be burned slowly to heat, e.g., an overhead chafing dish), automobile wax/polish, candles, furniture polish, metal cleaners/polishes, household cleaners, paint strippers and insecticide carriers.

Formulations to prepare such materials are well known in the art. For example, U.S. Pat. Nos. 3,615,289 and 3,645,705 describe the formulation of candles. U.S. Pat. Nos. 3,148,125 and 5,538,718 describe the formulation of lipstick and other cosmetic sticks. U.S. Pat. Nos. 4,275,054, 4,937,069, 5,069,897, 5,102,656 and 5,500,209 each describe the formulation of deodorant and/or antiperspirant.

The block copolymer of the invention may be incorporated into commercial products such as those listed above, as well as cable filling compounds, urethane/alkyl paint additives, and soaps/surfactants. These products may be prepared by blending the block copolymer with the other components of the product. In these commercial products, the block copolymer will typically be present at a concentration of about 1% to about 50% of the composition, based on the total weight of the composition. It is a routine matter to optimize the amount of block copolymer in a composition, and indeed the amount will vary depending on the actual product and the desired consistency of the product. In general, as more block copolymer is used in a formulation, the product will display a more pronounced gel character, and will form a more rigid, or hard, gel.

The following examples are offered by way of illustration and not by way of limitation.

EXAMPLES

In the following Examples, softening point was measured using a Model FP83HT Dropping Point Cell from Mettler Instruments, Mettler-Toledo International, Inc. (CH-8606 Greifensee, Switzerland; @mt.com), with a heating rate of 1.5° C./min. Techniques to measure acid and amine numbers are well known in the art and need not be described here. See, e.g., ASTM D-465 (1982) from American Society for Testing and Materials (West Conshohocken, Pa.; @astm.org).

EMPOL™ dimer acid was obtained from Henkel Company, and is now available from Cognis (@cognis.com). Ethylene diamine (EDA) is available from Aldrich (Milwaukee, Wis.; @sigma-aldrich.com). NEODOL™ alcohol ethoxylates are available from Shell Chemical Company (Houston, Tex.; @shell.com).

Example 1

Hydrocarbyl Ethoxylate-Terminated Block Copolymer

A mixture of 67.4 parts EMPOL™ 1008 dimer acid (100 eq. % of acid equivalents), 5.1 parts ethylene diamine (EDA) (72.2 eq. % of amine+hydroxyl equivalents, based on acid equivalents) and 27.4 parts NEODOL™ 23-6.5 alcohol ethoxylate (27.4 eq. % of amine+hydroxyl equivalents, based on acid equivalents) was prepared and heated to about 200-250° C. under a nitrogen atmosphere with simultaneous removal of water. A small amount (ca. 0.1-1.0 parts) hypophosphorous acid was added to minimize coloration of the product. Progress of the reaction was monitored by periodically pulling samples and measuring the acid and/or amine number of the product mixture. A nitrogen sparge was introduced to reduce the amine number to a desired level. The product block copolymer was characterized and found to have an acid number of 18.3 (higher than the theoretical value of 6, indicating incomplete reaction of the alcohol ethoxylate), an amine number of 1.1, a softening point of 90.3° C. and a viscosity at 160° C. of 85 cPs.

Example 2

Hydrocarbyl Ethoxylate-Terminated Block Copolymer

The procedure of Example 1 was followed using 57.6 parts EMPOL™ 1008 (100 eq. % acid), 4.4 parts EDA (71.7 eq. % amine+hydroxyl, based on acid equivalents) and 38.0 parts NEODOL™ 45-13 (23.9 eq. % amine+hydroxyl, based on acid equivalents). The product had an acid number of 16.9 (higher than the theoretical value of 6, indicating incomplete reaction of the alcohol ethoxylate), an amine number of 0.6, a softening point of 92° C. and a viscosity at 160° C. of 94 cPs. The softening point is approximately the same as the block copolymer of Example 1, indicating that ethoxylate molecular weight does not have a large impact on softening point. The gelling behavior of this block copolymer is described in Example 4.

Example 3

Hydrocarbyl Ethoxylate-Terminated Block Copolymer

The procedure of Example 1 was followed using 47.8 parts EMPOL™ 1008 (100 eq. % acid), 2.8 parts EDA (56.2 eq. % amine+hydroxyl, based on acid equivalents) and 49.4 parts NEODOL™ 45-13 (37.4 eq. % amine+hydroxyl, based on acid equivalents). The product had an acid number of 21.4 (higher than the theoretical value of 6, indicating incomplete reaction of the alcohol ethoxylate), an amine number of 0.4, a softening point of 83.7° C. and a viscosity at 160° C. of 67 cPs. The softening point and melt viscosity are both lower than that of the copolymer of Example 2, indicating that a higher degree of termination reduces the molecular weight of the block copolymer. The gelling behavior of this block copolymer is described in Example 4.

Example 4

Gelling Behavior of Hydrocarbyl Ethoxylate-Terminated Block Copolymer

The copolymers of Examples 2 and 3 were combined with various polar liquids at a 15 wt % copolymer concentration. The observed gelling properties of the hydrocarbyl-ethoxylate-terminated polyamides are described in TABLE F (TABLE F—GELATION PROPERTIES OF ETHOXYLATE-POLYAMIDES COPOLYMERS AT 15% RESIN). The gelling behavior indicates that the higher level of ethoxylate termination (Example 3) makes the resin more compatible with the polar liquids. This is demonstrated by the fact that the copolymer of Example 2 gels hexylene glycol to form a clear gel, 2-methoxyethyl ether to form an opaque gel, and forms two phases in dipropylene glycol; while the copolymer of Example 3 dissolves in hexylene glycol, forms a clear gel in methoxyethyl ether, and forms an opaque liquid in dipropylene glycol. This indicates that the gelling ability of these resins is a balance between their compatibility (ethoxylate content) and amide content (where amide content is directly proportional to the molecular weight of the resin). However, neither of the copolymers of Examples 2 or 3 was capable of gelling propylene glycol, polyethylene glycol, dipropylene glycol. This may be due to the hydrophobic alkyl chain within the ethoxylate molecule. In TABLE F, and elsewhere in the TABLES set forth herein, "ND" indicates "not determined".

TABLE F

| Gelation Properties of Ethoxylate-Polyamide Copolymers at 15% Resin | | |
|---|---|---|
| Polar Liquid | Example 2 | Example 3 |
| Hexylene glycol | Transl. Gel | Clear liquid |
| Propylene glycol | 2 phases | 2 phases |
| Polyethylene glycol (E-200) | 2 phases | 2 phases |
| Poly(ethylene glycol) dimethyl ether | Opaque gel | Opaque gel |
| Diethylene glycol ethyl ether | Opaque gel | N/D |
| Dipropylene glycol | 2 phases | Opaque liquid |
| 2-Methoxyethyl ether | Opaque gel | Clear gel |

Example 5

Hydrocarbyl Polyalkyl Glycol-Terminated Block Copolymer

The procedure of Example 1 was followed using 61.8 parts EMPOL™ 1008 (100 eq. % acid), 4.3 parts EDA (66.5 eq. % amine+hydroxyl, based on acid equivalents) and 33.9 parts MPEG 550 (28.5 eq. % amine+hydroxyl, based on acid equivalents). The product had an acid number of 20.5 (higher than the theoretical value of 6, indicating incomplete reaction of the alcohol ethoxylate), an amine number of 1.0, a softening point of 91° C. and a viscosity at 160° C. of 52 cPs. The gelling behavior of this block copolymer is described in Example 8. At high termination levels (see Examples 6 and 7), the properties of the block copolymer are dominated by the polyalkyl glycol.

Example 6

Hydrocarbyl Polyalkyl Glycol-Terminated Block Copolymer

The procedure of Example 1 was followed using 37.3 parts EMPOL™ 1008 (100 eq. % acid), 2.7 parts EDA (68.9 eq. % amine+hydroxyl, based on acid equivalents) and 59.9 parts MPEG 2000 (23.0 eq. % amine+hydroxyl, based on acid equivalents). The product had an acid number of 17.1 (higher than the theoretical value of 6, indicating incomplete reaction of the alcohol ethoxylate), an amine number of 0.4, a softening point of 75.4° C. and a viscosity at 160° C. of 224 cPs. The gelling behavior of this block copolymer is described in Example 8.

Example 7

Hydrocarbyl Polyalkyl Glycol-Terminated Block Copolymer

The procedure of Example 1 was followed using 26.1 parts EMPOL™ 1008 (100 eq. % acid), 1.6 parts EDA (56.5 eq. % amine+hydroxyl, based on acid equivalents) and 31.8 parts MBPPG 2500 (31.8 eq. % amine+hydroxyl, based on acid equivalents). The product had an acid number of 17.3 (higher than the theoretical value of 6, indicating incomplete reaction of the alcohol ethoxylate), an amine number of 0.5, a softening point of 41.9° C. and a viscosity at 160° C. of 35 cPs. The gelling behavior of this block copolymer is described in Example 8.

Example 8

Gelling Behavior of Hydrocarbyl Ethoxylate-Terminated Block Copolymer

The copolymers of Examples 5, 6 and 7 were combined with various polar liquids at a 15 wt % copolymer concentration. The observed gelling characteristics of these copolymers is given in TABLE G (TABLE G—GELATION PROPERTIES OF POLYALKYL GLYCOL-POLYAMIDE COPOLYMERS AT 15% RESIN). The copolymers of Examples 5 and 6 gelled hexylene glycol, but the copolymer of Example 6 gave an opaque gel. The opaque gel is likely caused by the MPEG 2000, which dissolves in hexylene glycol at elevated temperature, but crystallizes out when cooled. This result suggests that the terminal molecule is preferably a liquid that is soluble in the glycol, if a transparent gel is desired. The copolymer of Example 5 gelled the various polar liquids with combinations of hydroxyl and ether functionality, but was incompatible with polyethylene glycol and propylene glycol. This result suggests that the level of liquid terminator is desirably high in some instances.

However, at >70 wt % of a liquid terminator, the copolymer of Example 7 was a very soft opaque solid that was incompatible with propylene glycol. This behavior may be due to unreacted dimer in the resin that is incompatible with the glycol. Thus, the hydrocarbon-terminated polyalkyl glycol-polyamide block copolymers have excellent gelling properties when a liquid terminator is used and the level of termination is not too great. As with the hydrocarbon-terminated ethoxylate-polyamide copolymers, the gelling characteristics of these resins is a balance between the amide density and polyalkyl glycol content.

TABLE G

Gelation Properties of Polyalkyl Glycol-Polyamide Copolymers at 15% Resin

| Polar Liquid | Example 5 | Example 6 | Example 7 |
|---|---|---|---|
| Hexylene glycol | Clear gel | Opaque gel | ND |
| Propylene glycol | 2 phases | 2 phases | 2 phases |
| Polyethylene glycol (E-200) | 2 phases | 2 phases | ND |
| Diethylene glycol ethyl ether | Transl. gel | ND | ND |
| Poly(ethylene glycol) dimethyl ether | Opaque gel | ND | ND |
| 2-Methoxyethyl ether | Transl. gel | ND | ND |
| Dipropylene glycol | Opaque gel | ND | ND |

Example 9

Hydrocarbyl Oxa Acid-Terminated Block Copolymer

The procedure of Example 1 was followed using 74.4 parts EMPOL™ 1008 (75 eq. % acid, based on total acids), 15.7 3,6,9-trioxadecanoic acid (25 eq. % based on total acids) and 9.9 parts EDA (94.7 eq. % amine, based on acid equivalents). The product had an acid number of 11.6, an amine number of 1.1, a softening point of 88.1° C. and a viscosity at 183° C. of 35 cPs. The use of an oxa acid tends to provide a darker colored block copolymer, relative to the use of polyalkyl glycols and alcohol ethoxylates. The gelling behavior of this block copolymer is described in TABLE H below.

TABLE H

Gelation Properties of Oxa Acid-Polyamide Copolymer at 15% Resin

| Polar Liquid | Gel Description |
|---|---|
| 15% in hexylene glycol | Clear gel |
| 15% in Propylene glycol | 2 phases |
| 15% in polyethylene glycol (E-200) | 2 phases |
| 15% in diethylene glycol ethyl ether | Transl. Gel |
| 15% in dipropylene glycol | Opaque gel |
| 15% in poly(ethylene glycol) dimethyl ether | opaque liquid |
| 15% in 2-methoxyethyl ether | Opaque gel |

Examples 10-18

Hydrocarbyl Polyoxyalkyleneeamine-Polyamide Block Copolymer

The procedure of Example 1 was followed using EMPOL™ 1008, UNIDYME 18 dimer acid (from Arizona Chemical, Jacksonville, Fla.), EDA, hexamethylene diamine (HMDA, Aldrich), sebacic acid (sebacic, Aldrich), polyoxyalkyleneamine, etc. in the amounts shown in TABLE I. TABLE I also provides the acid number (AN), amine number (AM), softening point in ° C. (s.p. (° C.), molecular weight as determined by gel permeation chromatography using THF as the polar liquid and reported as both Mn and Mw by reference to polystyrene standards, and viscosity as measured in centipoise at 160° C. (Visc. @ 160° C. (cPs)) for the corresponding product.

Unlike the polyalkyl glycol-polyamide block copolymers, the reactants used to prepare the polyoxyalkyleneamine-polyamide block copolymers react almost completely with the terminator (theoretical acid number=6). Increasing the level of termination (Examples 14 and 13) resulted in a lower softening point and viscosity. The addition of HMDA lowers the softening point (Examples 13 and 17) relative to the use of EDA only, while the addition of sebacic acid as a co-diacid raised the softening point.

The diglycol amine polymer (Example 18) was made by reacting at 180° C. without vacuum in order to only react the amine and not the hydroxyl group. This material was made to determine the effect of free hydroxyl on the gelling characteristics.

The MW of the copolymers as determined by GPC indicates that the copolymers that contain JEFFAMINE™ M-2070 amine have number average MW's ($M_n$) of 4000 to 5000. This result indicates that these resins primarily comprise copolymers having either two or four amide groups, i.e., the resin is primarily a mixture of bis-amide and tetra-amide.

The gelling behavior of this group of block copolymers is described in TABLE J (TABLE J—GELATION PROPERTIES OF POLYOXYALKYLENE-AMINE-POLYAMIDE COPOLYMERS AT 15% RESIN). The copolymers terminated with high levels of >65 wt % M-2070 formed clear or transparent gels in all of the glycols, ethers, and polyols except hexylene glycol, where they dissolved. The addition of sebacic acid raised the softening point of the copolymer, but appeared to make the gels in propylene glycol feel softer. Decreasing the amount of termination (i.e., increasing the average molecular weight (MW) of the resin) resulted in firmer gels in propylene glycol, but the gels were transparent rather than clear. The use of HMDA versus EDA increased the hardness of the gels in propylene glycol. Thus, the clearest and hardest gels are obtained by using HMDA and the maximum level of termination possible.

Generally, the gel characteristics are related to the level of termination and the density of amide groups. The use of HMDA versus EDA increased the hardness of the gels in propylene glycol. Thus, the clearest and hardest gels are obtained by using HMDA and the maximum level of termination possible. Resins having high levels of M-2070 were slightly soluble in water (at concentrations up to about 3-4%). Thus, these resins are extremely hydrophilic materials and demonstrate some surfactant properties.

TABLE I

Composition and Properties of Polyoxyalkyleneamine-Polyamides

| Example No. | Composition (eq %/wt %) | AN/AM | s.p. (° C.) | MW (GPC) $M_n/M_w$ | Visc. @ 160° C. (cPs) |
|---|---|---|---|---|---|
| 10 | 100/60.0 EMPOL ™, 66.4/4.2 EDA, 28.5/35.8 XTJ 505 | 8.0/0.9 | 93 | | 68.5 |
| 11 | 100/48.4 EMPOL ™, 79.6/4.1 EDA, 14.1/47.6 XTJ 507 | 8.3/0.6 | 103.1 | | 225 |

TABLE I-continued

Composition and Properties of Polyoxyalkyleneamine-Polyamides

| Example No. | Composition (eq %/wt %) | AN/AM | s.p. (° C.) | MW (GPC) $M_n/M_w$ | Visc. @ 160° C. (cPs) |
|---|---|---|---|---|---|
| 12 | 100/22.5 EMPOL ™ 1008, 44.7/1.1 EDA, 48.5/76.4 JEFFAMINE ™ M-2070 | 7.1/0.5 | 89.2 | | 57.5 |
| 13 | 100/25.7 EMPOL ™, 47.6/1.3 EDA, 40.5/73.0 JEFFAMINE ™ M-2070 | 8.7/0.4 | 89 | 5264/7658 | 59.5 |
| 14 | 100/30.1 EMPOL ™, 57.5/1.8 EDA, 32.3/68.1 M-2070 | 6.2/0.6 | 98.2 | 5078/7804 | 75 |
| 15 | 90/24.6 EMPOL ™, 10/1.0 sebacic, 50.6/1.5 EDA, 38.2/73.0 M-2070 | 8.0/0.3 | 115.5 | 4733/7884 | 63 |
| 16 | 75/21.0 EMPOL ™, 25/2.5 sebacic, 50.8/1.5 EDA, 38.3/75.0 M-2070 | 6.9/0.6 | 140.9 | | 85 |
| 17 | 100/25.5 EMPOL ™, 47.5/2.5 HMDA, 40.5/72.1 M-2070 | 8.7/0.3 | 83 | 4325/7736 | 108 |
| 18 | 100/82.6 UNIDYME ™ 18, 52.9/4.5 EDA, 43.3/12.9 diglycol amine | 9.6/2.5 | 62.9 | 2004/4572 | 171 |

TABLE J

| Polar Liquid | Example 10 | Example 11 | Example 13 | Example 14 | Example 15 | Example 17 | Example 18 |
|---|---|---|---|---|---|---|---|
| Hexylene glycol | Clear gel | Transl. gel | Clear liq. | Clear liq. | Clear liq. | Clear liq. | Clear liq. |
| Propylene glycol | 2 phases | 2 phases | Clear gel | Transl. Gel | Clear gel | Clear gel | 2 phases |
| Ethylene glycol | ND | ND | ND | ND | ND | 2 phases | ND |
| Polyethylene glycol (E-200) | 2 phases | 2 phases | Clear gel | Clear gel | Clear gel | Transl. Gel | ND |
| Polyethylene glycol (E-300) | ND | ND | Clear gel | Clear gel | Clear gel | Clear gel | ND |
| Diethylene glycol ethyl ether | Clear gel | ND | ND | ND | ND | ND | ND |
| Dipropylene glycol | Opaque gel | Opaque gel | Clear gel | Transl. Gel | ND | Clear gel | ND |
| Poly(ethylene glycol) dimethyl ether | ND | Transl. Gel | Clear gel | ND | ND | Clear gel | ND |
| 2-methoxyethyl ether | ND | Transl. gel | Clear gel | Transl. gel | ND | Clear gel | Opaque gel |
| DESMOPHEN ™ 1600 U Linear polyether polyol | ND | ND | Clear gel | Transl. Gel | ND | ND | ND |
| DESMOPHEN ™ 550 U Branched polyether polyol | ND | ND | Clear gel | Clear gel | ND | ND | ND |

Examples 19-22

Hydrocarbyl Polyoxyalkyleneamine-Polyamide Block Copolymer

Four resins of the invention were prepared, essentially according to the procedure of Example 1, having the compositions, physical properties and gelation properties as set forth in Table K (Composition and Properties of Poly(oxyalkylene) Monoamine Terminated Polyamides Containing No Co-Diamine).

Examples 23-32

Hydrocarbyl Polyoxyalkyleneamine-Polyamide Block Copolymer

A series of resins was prepared having varying amounts of ethylene diamine and polyetherdiamine (specifically XTJ-504, formerly JEFFAMINE® EDR-148). The reactants for these resins, as well as the physical properties and gelation properties of the resin, are set forth in TABLE L (Composition and Properties of Poly(oxyalkylene) Monoamine-terminated Polyamides Containing JEFFAMINE® EDR-148).

TABLE K

Composition and Properties of Poly(oxyalkylene) Monoamine Terminated Polyamides Containing No Co-Diamine

| Example No. | Resin Composition EMPOL 1008 - M2070 - EDA (weight %) | AN/AM | Termination Eq. % on Dimer | Co-Diamine Fraction Total Diamines, Eq. | Propylene Glycol Cut (20 wt %) |
|---|---|---|---|---|---|
| 19 | 22.5 - 76.3 - 1.1 | 2.9/0.6 | 47.8 | 0 | Clear jelly |
| 20 | 25.1 - 73.3 - 1.6 | N.D. | 41.2 | 0 | Clear gel * |
| 21 | 27.1 - 71.1 - 1.8 | N.D. | 37.0 | 0 | Sl. hazy gel * |
| 22 | 24.0 - 74.7 - 1.4 | 1.6/N.D. | 44.0 | 0 | Sl. hazy gel * |

These resins were prepared by heating about 100 g of the ingredients (total charge) in a 250 mL Erlenmeyer flask in the presence of three drops of 25% aqueous hypophosphorous acid under a gentle nitrogen sweep with stirring. After the mixture reached 220° C., it was held at that temperature for about 3 h. All of these resins were nearly water white in color. All of these resins are soft to one degree or another; in general, the higher the polyalkyleneoxy content, the softer the resin.

TABLE L

Composition and Properties of Poly(oxyalkylene) Monoamine-terminated Polyamides Containing XTJ-504

| Example No. | Resin Composition EMPOL 1008 - M-2070 - EDA - XTJ-504 (weight %) | Termination Eq. % on Dimer | Co-Diamine Eq. % Total Eq. Diamines | Propylene Glycol Cut (20 wt %) |
|---|---|---|---|---|
| 23 | 26.8 - 70.3 - 0.9 - 2.0 | 37.0 | 46.0 | Clear, weak jelly |
| 24 | 31.1 - 65.2 - 1.4 - 2.2 | 29.6 | 39.4 | Clear jelly |
| 25 | 35.4 - 60.4 - 1.8 - 2.4 | 24.1 | 34.9 | Clear firm gel |
| 26 | 52.4 - 39.3 - 2.4 - 6.0 | 10.6 | 50.0 | Sl. hazy firm gel |
| 27 | 79.6 - 0 - 0 - 20.4 | 0 | 100 | Incompatible |
| 28 | 42.0 - 52.0 - 2.0 - 4.0 | 17.5 | 44.8 | Clear gel |
| 29 | 82.9 - 0 - 2.7 - 14.4 | 0 | 68.0 | Incompatible |
| 30 | 64.3 - 20.0 - 0 - 15.7 | 4.4 | 100 | Incompatible |
| 31 | 58.5 - 30.0 - 1.6 - 9.9 | 7.2 | 71.3 | Cloudy paste |
| 32 | 45.3 - 46.6 - 1.3 - 6.8 | 14.5 | 53.4 | Clear jelly |

A preferred range of termination, using M-2070, is about 15-18 eq. % with a co-diamine level of about 45-48 eq. % (more than this results in a clear, but mobile "jelly").

Examples 33-38

Hydrocarbyl Polyoxyalkyleneeamine-Polyamide Block Copolymer

A series of resins was prepared having varying amounts of ethylene diamine and polyetherdiamine (specifically JEFFAMINE® D-400). The reactants for these resins, as well as the physical properties and gelation properties of the resin, are set forth in Table M (Composition and Properties of Poly (oxyalkylene) Monoamine-terminated Polyamides Containing JEFFAMINE® D-400.

These resins were prepared by heating about 100 g of the specified ingredients (total charge) in a 250 mL Erlenmeyer flask in the presence of three drops of 25% aqueous hypophosphorous acid under a gentle nitrogen sweep with stirring. After the mixture reached 220° C., it was held at that temperature for about 3 h. All of the resulting resins were nearly water white in color. All of these resins were soft to one degree or another; in general, the higher the polyalkyleneoxy content, the softer the resin.

TABLE M

Composition and Properties of Poly(oxyalkylene) Monoamine-terminated Polyamides Containing JEFFAMINE ® D-400

| Ex. No. | Resin Composition EMPOL 1008 - M2070 - EDA - Jeff. D400 (weight %) | AN/AM | Termination Eq. % on Dimer | Co-Diamine Fraction Total Diamines, Eq. | Propylene Glycol Cut (20 wt %) |
|---|---|---|---|---|---|
| 33 | 45.3 - 46.6 - 1.3 - 6.8 | —/— | 16.9 | 36.7 | Clear weak gel |
| 34 | 35.6 - 55.9 - 2.0 - 6.4 | 2.8/0.6 | 22.2 | 30.3 | Clear firm gel |
| 35 | 35.9 - 55.6 - 2.0 - 6.4 | 3.2/1.3 | 21.9 | 30.2 | Clear firm gel |
| 36 | 59.3 - 24.7 - 4.2 - 11.9 | 4.5/0.8 | 5.9 | 28.1 | Cloudy firm gel |
| 37 | 69.8 - 13.8 - 5.6 - 10.8 | —/— | 2.8 | 20.9 | Incompatible |
| 38 | 59.4 - 24.6 - 4.2 - 11.8 | 4.4/0.6 | 5.9 | 28.0 | nd |

Formulations of dimer acid, EDA, M-2070, and D-400 gel propylene glycol over a wide range of compositional space, from about 45-60 wt % dimer, 47-25% monoamine, and 6-12% D-400, adjusted to have a termination level of 6-22 eq. % with about 30-35% eq. replacement of EDA with D-400.

Such resins, and formulations to prepare such resins, are a preferred embodiment of the present invention. For instance, in one aspect, the present invention provides a product prepared by a process of condensing reactants comprising polyoxyalkyleneamine, polyoxyalkylenediamine and dimer acid, to provide a hydrocarbon-terminated block copolymer having a number average molecular weight of less than 10,000. The polyoxyalkyleneamine may have the formula R—O—[(R$^a$—O)$_n$—(R$^b$—O)$_m$]—R$^c$—NH$_2$ where (R$^a$—O)$_n$—(R$^b$—O)$_m$ represents a plurality of R$^a$—O and R$^b$—O units arranged in any sequence, the sum of n and m provides a molecular weight of 1,500 to 2,500 g/mol and either m or n may be zero, R is $C_1$-$C_6$alkyl, $R^a$ is —$CH_2CH_2$—, $R^b$ is —$CH(CH_3)$—$CH_2$—, and $R^c$ is selected from $R^a$ and $R^b$. The polyoxyalkyeneamine may have the structure of JEFFAMINE M2070. The polyoxyalkyenediamine may have the formula $H_2N$—$[(R^a$—$O)_n$—$(R^b$—$O)_m]$—$R^c$—$NH_2$ where $(R^a$—$O)_n$—$(R^b$—$O)_m$ represents a plurality of $R^a$—$O$ and $R^b$—$O$ units arranged in any sequence, the sum of n and m provides a molecular weight of 200 to 800 g/mol and either m or n may be zero, $R^a$ is —$CH_2CH_2$—, $R^b$ is —$CH(CH_3)$—$CH_2$—, and $R^c$ is selected from $R^a$ and $R^b$. The polyoxyalkylenediamine may have the structure of Jeffamine D-400. The final product is resin that preferably has an acid number of less than 10 and an amine number of less than 10. In a preferred embodiment, the reactants further comprise ethylene diamine, as shown in TABLE M. Thus, in one aspect, the polyoxyalkyleneamine contributes 25-47 wt % % of the reactants, polyoxyalkylenediamine contributes 6-12 wt % of the reactants, and dimer acid contributes 45-60 wt % of the reactants. In another aspect, polyoxyalkyleneamine contributes 25-47 wt % of the reactants, polyoxyalkylenediamine contributes 6-12 wt % of the reactants, dimer acid contributes 45-60 wt % of the reactants, and ethylene diamine contributes 1-6 wt % of the reactants.

Examples 39-45

Hydrocarbyl Polyoxyalkyleneamine-Polyamide Block Copolymer

A series of resins was prepared having varying amounts of ethylene diamine and polyetherdiamine (specifically HUNTSMAN XTJ-500 and/or HUNTSMAN XTJ-506). The reactants for these resins, as well as the physical properties and gelation properties of the resin, are set forth in Table N (Composition and Properties of Poly(oxyalkylene) Monoamine-terminated Polyamides Containing HUNTSMAN XTJ-500 and/or HUNTSMAN XTJ-506.)

These resins were prepared by heating about 100 g of the specified reactants (total charge) in a 250 mL Erlenmeyer flask in the presence of three drops of 25% aqueous hypophosphorous acid under a gentle nitrogen sweep with stirring. After the mixture reached 220° C., it was held at that temperature for about 3 h. All of the resulting resins were nearly water white in color. All of these resins were soft to one degree or another; in general, the higher the polyalkyleneoxy content, the softer the resin.

The resin of Example 45 represents a block copolymer of the present invention with a high molecular weight and viscosity that still exhibits useful gelation properties, although it is incompatible with propylene glycol. It had a softening point of 96.8° C., MWw of 18,240 daltons and a viscosity at 160° C. of 2,940 cPs. It dissolves in and forms a clear, firm gel with the polar liquid ethyl lactate.

TABLE N

Composition and Properties of Poly(oxyalkylene) Monoamine-terminated Polyamides Containing Huntsman XTJ-500 and/or XTJ-506

| Ex. No. | Resin Components & Composition | Termination Eq. % on Dimer | Co-Diamine Fraction Total Diamines, Eq. | Propylene Glycol Cut (20 wt %) |
|---|---|---|---|---|
| Empol 1008 - M2070 - EDA - XTJ500 (wt %) | | | | |
| 39 | 56.0 - 23.0 - 3.8 - 17.2 | 5.8 | 30.0 | Cloudy firm gel |
| Empol 1008 - XTJ506 - EDA - Jeff. D400 (wt %) | | | | |
| 40 | 59.8 - 25.2 - 3.9 - 11.1 | 12.0 | 28.0 | nd |
| 41 | 42.0 - 49.3 - 2.1 - 6.6 | 33.5 | 29.6 | Clear firm gel |
| 42 | 69.9 - 12.6 - 5.1 - 25.0 | 5.1 | 25.1 | Incompatible |
| Empol 1008 - XTJ506 - EDA - XTJ500 (wt %) | | | | |
| 43 | 63.3 - 15.6 - 4.5 - 16.6 | 7.0 | 25.9 | Incompatible |
| 44 | 73.9 - 4.2 - 6.0 - 16.0 | 1.6 | 20.3 | Incompatible |
| 45 | 70.0 - 6.5 - 5.2 - 18.2 | 2.7 | 20.3 | Incompatible |

Examples 46-52

Gellant Resins

The components listed below in TABLE O were charged in the amounts shown to a 250 mL glass reactor equipped with a stirrer, thermocouple probe, nitrogen gas inlet and vapor outlet to a condenser. The reaction mixture was heated rapidly under a gentle sweep of nitrogen to about 120-130° C. at which point stirring of the liquefied mass was begun. Heating was continued and water vapor began appearing in the condenser trap at about 150° C. Heating was continued to bring the reaction mixture to a top temperature of about 220° C. After about 6-7 hours at that temperature, the product was discharged and tested for acid and amine number and ring & ball softening point.

TABLE O

Composition and Properties of Dimer Acid-Based Gellant Resin Compositions

| Component | Example 46 Wt. % | Example 47 Wt. % | Example 48 Wt. % | Example 49 Wt. % | Example 50 Wt. % | Example 51 Wt. % | Example 52 Wt. % |
|---|---|---|---|---|---|---|---|
| EMPOL ™ 1008 dimer acid | 63.3 | 63.3 | 62.9 | 63.2 | 63.6 | 59.6 | 56.0 |
| Ethylene Diamine | 4.5 | 4.7 | 5.1 | 4.9 | 4.4 | 4.1 | 3.8 |
| JEFFAMINE ™ M-2070 amine | — | 20.0 | 20.0 | — | — | 24.6 | 23.0 |
| Huntsman XTJ-506 ™ amine | 15.6 | — | — | 20.0 | 21.0 | — | — |
| JEFFAMINE ™ D-400 amine | — | 12.0 | — | — | 12.6 | 11.7 | — |

TABLE O-continued

Composition and Properties of Dimer Acid-Based Gellant Resin Compositions

| Component | Example 46 Wt. % | Example 47 Wt. % | Example 48 Wt. % | Example 49 Wt. % | Example 50 Wt. % | Example 51 Wt. % | Example 52 Wt. % |
|---|---|---|---|---|---|---|---|
| Huntsman XTJ-500 ™ amine | 16.6 | — | 12.0 | 12.0 | — | — | 17.2 |
| Softening Point | 92.0 | 98.7 | 101.5 | 101.5 | 97.5 | 96.3 | n.d |
| Acid Number | 5.3 | 4.5 | 2.5 | 5.4 | 10.4 | 5.0 | n.d |
| Amine Number | 0.5 | 1.0 | 2.5 | 1.2 | 0.4 | 0.7 | n.d |

The gellant resins of Examples 46-52 were tested as gellants for the liquids listed in TABLE P by heating 3.0 g resin and 17.0 g liquid to about 100° C. with stirring. In almost all cases, the mixture became homogeneous and clear upon heating and was then poured into a sample vial and allowed to cool completely at room temperature. The mixture was evaluated by inverting the vial with gentle shaking. If the mixture did not move at all it was classed as "gel". If it moved as a mass or broke into smaller masses and moved, it was classed as "jelly". In some cases, the liquid flowed freely, in which case the resin was classed as "soluble". The clarity of the mass was also evaluated and classed as "clear" (transparent), "hazy" (translucent), or "cloudy" (essentially opaque). In some cases, the mass cooled into a two-phase (solid-liquid) paste and was classed as "incompatible".

TABLE Q

CHDA-Based Resin Compositions

| Component | Example 53 Wt. % | Example 54 Wt. % | Example 55 Wt. % |
|---|---|---|---|
| Cyclohexane Dicarboxylic Acid | 21.7 | 17.7 | 19.6 |
| JEFFAMINE ™ M-2070 amine | 25.6 | 41.9 | 23.1 |
| JEFFAMINE ™ D-400 amine | 52.6 | 40.3 | 23.6 |
| Huntsman XTJ-500 amine | — | — | 33.8 |
| Softening Point | 129.6 | 141.9 | 119.0 |
| Acid Number | 6.4 | 5.2 | 9.3 |
| Amine Number | 1.0 | 0.9 | 1.5 |

TABLE P

Gelation Ability of Dimer Acid-Based Resin Compositions

| Polar Liquid | Example 46 | Example 47 | Example 48 | Example 49 | Example 50 | Example 51 | Example 52 |
|---|---|---|---|---|---|---|---|
| Butyl Acrylate | — | — | — | — | — | — | Clear gel |
| Butyl Propionate | Clear gel | — | — | — | — | Clear gel | Clear gel |
| Cyclohexanone | Clear gel | — | — | — | — | Clear gel | Clear gel |
| Dibutyl Adipate | Hard, hazy Gel | Hard, hazy gel | Hard, hazy gel | Hard, hazy gel | Hard, hazy gel | Slightly hazy gel | Clear gel |
| Dichloroethane | — | Clear gel | Clear gel | Clear gel | Soft, clear gel | — | Clear gel |
| Dimethyl Sulfoxide | — | Clear gel | — | — | Incompatible | — | Clear gel |
| Dowanol DPM | Slght hazy gel | Clear gel | Clear gel | Soft, clear gel | Soft, clear gel | Clear gel | Clear gel |
| Dowanol EPH | Clear jelly | Soft, clear gel | Soft, clear gel | Soft, clear gel | Weak jelly | Clear jelly | Clear jelly |
| Ethoxyethyl Propionate | Hard, hazy gel | — | — | — | — | Cloudy gel | Clear gel |
| Ethyl Acetate | Hard, hazy gel | — | — | — | — | — | — |
| Ethyl Lactate | Clear gel | Slighty hazy gel | Clear gel | Soft, clear gel | Soft, clear gel | Clear gel | Clear gel |
| Methyl Ethyl Ketone | Slght hazy gel | — | — | — | — | — | — |
| N-Methyl Pyrolidinone | Soluble | Soft, clear gel | Soft, clear gel | Soft, clear gel | Soluble | Soft, clear gel | Clear jelly |
| Propylene Carbonate | Incompatible | — | — | — | — | Incompatible | Clear gel |
| Vinyl Propionate | — | — | — | — | — | — | Slightly hazy gel |
| Xylene | Clear gel | Clear gel | Clear gel | Soft, clear gel | Weak jelly | Clear gel | Clear gel |

Examples 53-55

CHDA-Based Gellant Resin Compositions

The components listed below in TABLE Q were reacted as in Examples 46-52 above to yield cyclohexane dicarboxylic acid (CHDA) resins Examples # 53-55, which were tested at 15% resin solids as described above for gelation ability with the results given in TABLE R.

TABLE R

Gelation Ability of CHDA-Based Resin Compositions

| Polar Liquid | Example 53 | Example 54 | Example 55 |
|---|---|---|---|
| Butyl Propionate | — | Clear gel | Incompatible |
| Cyclohexanone | Clear jelly | Weak jelly | Soluble |
| Dibutyl Adipate | Clear gel | Clear gel | Clear gel |
| Dichloroethane | Soluble | — | — |
| Dimethyl Sulfoxide | — | Soluble | Soluble |
| Dowanol DPM | Clear gel | Clear gel | — |
| Dowanol EPH | — | Soluble | Soluble |
| Dowanol TPG | — | — | Clear gel |
| Ethoxyethyl Propionate | Hazy gel | Clear gel | Hard, hazy gel |
| Ethyl Acetate | Slght hazy gel | — | — |

TABLE R-continued

Gelation Ability of CHDA-Based Resin Compositions

| | Test Resin | | |
|---|---|---|---|
| Polar Liquid | Example 53 | Example 54 | Example 55 |
| Ethyl Lactate | Soluble | Soluble | Soluble |
| Methyl Ethyl Ketone | Clear gel | — | — |
| N-Methyl Pyrolidinone | Soluble | Soluble | Soluble |
| Propylene Carbonate | Cldy gel | Hazy gel | Clear gel |
| Xylene | Clear paste | Clear gel | Weak jelly |

Example 56

Gelation of Epoxy Resins

A 3% solution of Example Resin #47 was prepared in EPON™ 828 liquid epoxy resin from Resolution, Inc. (formerly marketed by Shell). The mixture, when cooled to room temperature, was a homogeneous, slightly hazy, highly viscoetastic fluid. The starting liquid epoxy had a Brookfield viscosity of 76 cP (80° C.)/1,400 cP (40° C.) but the viscosity of the 3% resin blend was too high to be measured below about 80° C. Gel formation was reversible above about 85° C.; at 90° C. the low-shear rate Brookfield viscosity of the blend was 92 cP (at 5.6 s$^{-1}$) and at 85° C. increased to 1,900 cP (at 1.4 s$^{-1}$). Further cooling of the sample to 80° C. resulted in an increase in viscosity of the sample to 7,250 cP (at 0.3 s$^{-1}$). These very large increases in viscosity upon cooling signal the onset of gel formation. When the sample was heated back to 90° C., the viscosity gradually decreased (over about 30 minutes) to 218 cP.

Example 57

Gelation of Epoxy Resins

A 4% solution of Example Resin #55 was prepared in EPON™ 828 liquid epoxy resin as described in Example 56. The mixture, when cooled to room temperature, was a homogeneous, clear, highly viscous liquid, significantly more viscous than the EPON™ 828 liquid epoxy resin itself.

Example 58

Gelation of Neat Fragrance

A 5% solution of Example Resin #47 was prepared in liquid Fragrance No. 005823, a neat imitation apple essence from Bush Boake Allen (a division of International Fragrance and Flavors). The mixture, when cooled to room temperature, was a homogeneous, clear jelly. At a concentration of 9.5% Resin #47, the mixture became a clear gel.

All publications and patent applications mentioned in this specification are herein incorporated by reference to the same extent as if each individual publication or patent application was specifically and individually incorporated by reference. This includes, but is not limited to, U.S. patents, U.S. patent application publications, U.S. patent applications, foreign patents, foreign patent applications and non-patent publications referred to in this specification and/or listed in the Application Data Sheet.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A copolymer of the formula:

$$R^1 \!-\!\!\left(\!O\!-\!R^2\right)_{\!x}\!\!ZC(O)\!-\!\!\left(\!R^3\!-\!C(O)NH\!-\!R^4\!-\!HNC(O)\!\right)_{\!y}\!\!R^3\!-\!CZ\!-\!\left(\!R^2\!-\!O\right)_{\!z}\!\!R^1$$

wherein, independently,

R$^1$ is C$_{1-8}$ a hydrocarbon radical;

R$^2$ is a C$_2$-C$_4$ hydrocarbon diradical;

R$^3$ is a C$_2$-C$_{52}$ hydrocarbon diradical, wherein at least 50% of the diradicals are derived from dimer acid;

R$^4$ is selected from C$_2$-C$_8$ hydrocarbon diradicals and polyether diradicals of the formula: —(R$^{11}$—O)$_g$—R$^{11}$—, wherein R$^{11}$ is a C$_2$-C$_4$ hydrocarbon diradical independently selected at each occurrence and g is an integer ranging from 2 to 50;

Z is selected from O and NH;

x and z are integers from 2 to 100; and y is an integer equal to 1 or more that provides a copolymer molecular weight of from 2,000 to 50,000.

2. The copolymer according to claim 1, wherein, independently, R$^1$ is CH$_3$ and Z is NH.

3. The copolymer according to claim 1, wherein y is an integer from 1 to 10.

4. The copolymer according to claim 1, wherein y is an integer equal to 1 or more that provides a copolymer number average molecular weight of from 2,000 to 50,000.

5. A composition, comprising the copolymer according to claim 1; and at least one polar liquid.

6. The composition according to claim 5, comprising from 5 to 50 wt % of the copolymer.

7. The composition according to claim 5, wherein the at least one polar liquid comprises an ester-containing liquid.

8. The composition according to claim 7, wherein the at least one polar liquid comprises an ester-containing liquid having formula R$_6$—CO$_2$—R$_6$ or R$_6$—CO$_2$—R$_7$—CO$_2$—R$_6$, wherein R$_6$ and R$_7$ are organic moieties having from 1 to 12 carbon atoms.

9. The composition according to claim 8, wherein R$_6$ is selected from C$_1$-C$_{12}$ alkyl, C$_1$-C$_{12}$ hydroxy-substituted alkyl, C$_1$-C$_{12}$ alkoxy-substituted C$_1$-C$_{12}$ alkyl, C$_6$-C$_{12}$ aryl-substituted C$_{1-2}$ alkyl, C$_{1-12}$ alkenyl, C$_{1-12}$ hydroxyalkenyl, C$_{1-12}$ alkoxy-substituted C$_1$-C$_{12}$ alkenyl, C$_6$-C$_{12}$ aryl, C$_1$-C$_{12}$ alkyl-substituted C$_6$-C$_{12}$ amyl, C$_6$-C$_{12}$ hydroxy-substituted aryl, and C$_6$-C$_{12}$ alkoxy-substituted C$_6$-C$_{12}$ aryl, and R$_7$ is selected from C$_1$-C$_{12}$ alkylene, C$_1$-C$_{12}$ hydroxy-substituted alkylene, C$_2$-C$_{12}$ alkenylene, C$_6$-C$_{12}$ arylene, C$_6$-C$_{12}$ hydroxy-substituted arylene, and C$_1$-C$_{12}$ alkoxy-substituted C$_6$-C$_{12}$ arylene.

10. The composition according to claim 7, wherein the ester-containing liquid comprises at least one aromatic ester.

11. The composition according to claim 10, wherein the aromatic ester is at least one member selected from the group consisting of a (C$_1$-C$_{18}$ alkyl)benzoate, a (C$_1$-C$_{18}$ alkyl) salicylate, and a di(C$_1$-C$_{12}$ alkyl) phthalate.

12. The composition according to claim 5, wherein the at least one polar liquid comprises at least one member selected from the group consisting of a lower alcohol, glycol, ether, glycol ether, polyalkyleneglycol ether, and polyol.

13. The composition according to claim 5, wherein the at least one polar liquid comprises at least one member selected from the group consisting of propylene glycol, 2-methoxyethyl ether, diethylene glycol ethyl ether, ethylene glycol, hexylene glycol, ethylene glycol monophenyl ether, di(propylene glycol), di(propylene glycol) monomethyl ether, di(ethylene glycol) dimethyl ether, tripropylene glycol mono methyl ether, poly(ethylene glycol) and poly(propylene glycol).

14. The composition according to claim 5, wherein the at least one polar liquid comprises from 5 to 90 wt % of at least one surfactant based upon the total weight of the surfactant and copolymer.

15. The composition according to claim 5, wherein the polar liquid comprises an aromatic liquid.

16. The composition according to claim 15, wherein the aromatic liquid is at least one member selected from the group consisting of a ($C_1$-$C_{18}$ alkyl)benzoate, a ($C_1$-$C_{18}$ alkyl) salicylate, and a di($C_1$-$C_{12}$ alkyl) phthalate.

17. A personal care product, comprising any one of the compositions according to any one of claims 5 to 16; and a colorant.

18. An antiperspirant, comprising the copolymer according to claim 1; and
at least one member selected from the group consisting of aluminum chlorohydrate, aluminum sesquichlorohydrate, aluminum dichlorohydrate, aluminum-zirconium chlorohydrates, and aluminum-zirconium polychlorohydrate complexed with glycine.

19. A lipstick, comprising the copolymer according to claim 1;
at least one polar liquid; and at least one colorant.

20. A sun care product, comprising the copolymer according to claim 1;
at least one ($C_1$-$C_{18}$ alkyl) salicylate; and at least one surfactant.

21. The sun care product according to claim 20, further comprising at least one ester-containing liquid.

22. An eye make-up product, foundation makeup product, or costume make-up product, comprising the copolymer according to claim 1; at least one ester-containing liquid; and at least one colorant.

23. A wax, polish, cleaner, or stripper, comprising the copolymer according to claim 1; and at least one ester-containing liquid.

24. A wax, polish, cleaner, or stripper, comprising the copolymer according to claim 1; and at least one aprotic liquid.

25. The wax, polish, cleaner, or stripper according to claim 24, comprising from 5 to 90 wt % of at least one aprotic liquid based upon the total weight of the aprotic liquid and copolymer.

26. The wax, polish, cleaner, or stripper according to claim 25, wherein the at least one aprotic liquid is at least one member selected from the group consisting of N-methyl pyrrolidinone, propylene carbonate, tetrahydrofuran, dimethyl sulfoxide, methylene chloride, and dichloroethane.

27. A fragrance emitting article, comprising the copolymer according to claim 1; and at least one polar liquid wherein the polar liquid comprises at least one member selected from the group consisting of a liquid fragrance, an essential oil, and a fragrance chemical.

28. The fragrance emitting article according to claim 27, comprising from 10 to 90 wt % of the at least one polar liquid based upon the total weight of the copolymer and polar liquid.

29. The fragrance emitting article according to claim 27, comprising from 5 to 50 wt % of the copolymer based upon the total weight of the article.

30. The fragrance emitting article according to claim 27, wherein the at least one polar liquid further comprises at least one ester-containing liquid.

31. The fragrance emitting article according to any one of claim 27 to 30, wherein the at least one polar liquid further comprises at least one member selected from the group consisting of a lower alcohol, glycol, ether, glycol ether, polyalkyleneglycol ether, and polyol.

* * * * *